(12) United States Patent
Badie et al.

(10) Patent No.: US 12,161,474 B2
(45) Date of Patent: Dec. 10, 2024

(54) METHODS, DEVICES AND SYSTEMS FOR IDENTIFYING FALSE R-R INTERVALS AND FALSE ARRHYTHMIA DETECTIONS DUE TO R-WAVE UNDERSENSING OR INTERMITTENT AV CONDUCTION BLOCK

(71) Applicant: Pacesetter, Inc., Sylmar, CA (US)

(72) Inventors: Nima Badie, Berkeley, CA (US); Fujian Qu, San Jose, CA (US); Jong Gill, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 854 days.

(21) Appl. No.: 17/319,847

(22) Filed: May 13, 2021

(65) Prior Publication Data

US 2021/0369176 A1    Dec. 2, 2021

Related U.S. Application Data

(60) Provisional application No. 63/043,932, filed on Jun. 25, 2020, provisional application No. 63/033,815, filed on Jun. 2, 2020.

(51) Int. Cl.
*A61B 5/352* (2021.01)
*A61B 5/00* (2006.01)
(Continued)

(52) U.S. Cl.
CPC ............ *A61B 5/352* (2021.01); *A61B 5/0006* (2013.01); *A61B 5/361* (2021.01); *A61B 5/363* (2021.01);
(Continued)

(58) Field of Classification Search
None
See application file for complete search history.

(56) References Cited

U.S. PATENT DOCUMENTS 4,364,397 A    12/1982  Citron et al.
5,755,739 A     5/1998  Sun et al.
(Continued)

FOREIGN PATENT DOCUMENTS

CN    105326477 A    2/2016
EP      1615693 B1    1/2011
(Continued)

OTHER PUBLICATIONS

Response to Extended European Search Report dated Dec. 14, 2021, European Patent Application No. 21175590.5-1122.
(Continued)

*Primary Examiner* — Shirley X Jian
(74) *Attorney, Agent, or Firm* — Vierra Magen Marcus LLP

(57) ABSTRACT

Described herein are methods, devices, and systems for identifying false R-R intervals, and false arrhythmia detections, resulting from R-wave undersensing or intermittent AV conduction block. Each of one or more of the R-R intervals is classified as being a false R-R interval in response to a duration the R-R interval being greater than a first specific threshold, and the duration the R-R interval being within a second specified threshold of being an integer multiple of at least X other R-R intervals for which information is obtained, wherein the integer multiple is at least 2, and wherein X is a specified integer that is 1 or greater. When performed for R-R intervals in a window leading up to a detection of a potential arrhythmic episode, results of the classifying can be used to determine whether the potential arrhythmic episode was a false positive detection.

20 Claims, 8 Drawing Sheets

(51) Int. Cl.
*A61B 5/361* (2021.01)
*A61B 5/363* (2021.01)
*G16H 10/65* (2018.01)
*G16H 40/20* (2018.01)
*G16H 40/67* (2018.01)
*G16H 50/20* (2018.01)
*G16H 50/70* (2018.01)
*G16H 70/60* (2018.01)
*A61N 1/365* (2006.01)
*A61N 1/39* (2006.01)

(52) U.S. Cl.
CPC .............. *G16H 10/65* (2018.01); *G16H 40/20* (2018.01); *G16H 40/67* (2018.01); *G16H 50/20* (2018.01); *G16H 50/70* (2018.01); *G16H 70/60* (2018.01); *A61N 1/36507* (2013.01); *A61N 1/3956* (2013.01)

(56) References Cited

U.S. PATENT DOCUMENTS

| | | | |
|---|---|---|---|
| 6,512,946 B1 | 1/2003 | Hahn et al. | |
| 7,167,747 B2 | 1/2007 | Gunderson et al. | |
| 7,218,966 B2 | 5/2007 | Haefner | |
| 7,266,409 B2 | 9/2007 | Gunderson | |
| 7,283,863 B2 | 10/2007 | Gunderson et al. | |
| 7,333,855 B2 | 2/2008 | Gunderson et al. | |
| 7,412,282 B2 | 8/2008 | Houben | |
| 7,537,569 B2 * | 5/2009 | Sarkar .................... | A61B 5/363 600/515 |
| 7,582,061 B2 | 9/2009 | Li et al. | |
| 7,623,911 B2 | 11/2009 | Sarkar et al. | |
| 7,630,756 B2 | 12/2009 | Linker | |
| 7,634,310 B2 | 12/2009 | Lee et al. | |
| 7,774,049 B2 | 8/2010 | Ghanem et al. | |
| 7,774,062 B2 | 8/2010 | Kim et al. | |
| 7,783,354 B2 | 8/2010 | Gunderson | |
| 7,818,056 B2 | 10/2010 | Kim et al. | |
| 7,831,301 B2 | 11/2010 | Cao et al. | |
| 7,894,893 B2 | 2/2011 | Kim et al. | |
| 7,912,545 B2 | 3/2011 | Li et al. | |
| 8,078,277 B2 | 12/2011 | Gunderson et al. | |
| 8,160,686 B2 | 4/2012 | Allavatam et al. | |
| 8,260,404 B1 | 9/2012 | Bharmi et al. | |
| 8,265,737 B2 | 9/2012 | Warren et al. | |
| 8,406,872 B2 | 3/2013 | Stadler et al. | |
| 8,437,840 B2 | 5/2013 | Patel et al. | |
| 8,437,851 B2 | 5/2013 | Corbucci et al. | |
| 8,473,042 B2 | 6/2013 | McCarthy et al. | |
| 8,506,500 B2 | 8/2013 | Li et al. | |
| 8,521,281 B2 | 8/2013 | Patel et al. | |
| 8,538,524 B2 | 9/2013 | Rosenberg et al. | |
| 8,560,058 B2 | 10/2013 | Babaeizadeh et al. | |
| 8,560,069 B2 | 10/2013 | Zhang | |
| 8,577,455 B2 | 11/2013 | Mitrani et al. | |
| 8,583,221 B1 | 11/2013 | Patel et al. | |
| 8,588,895 B2 | 11/2013 | Sanghera et al. | |
| 8,588,896 B2 | 11/2013 | Allavatam et al. | |
| 8,626,280 B2 | 1/2014 | Allavatam et al. | |
| 8,639,316 B2 | 1/2014 | Sarkar | |
| 8,744,559 B2 | 6/2014 | Houben et al. | |
| 8,750,994 B2 | 6/2014 | Ghosh et al. | |
| 8,774,909 B2 | 7/2014 | Patel et al. | |
| 8,781,585 B2 | 7/2014 | Gunderson et al. | |
| 8,792,971 B2 | 7/2014 | Gunderson et al. | |
| 8,886,296 B2 | 11/2014 | Patel | |
| 8,897,863 B2 | 11/2014 | Linker | |
| 8,914,106 B2 | 12/2014 | Charlton et al. | |
| 8,942,793 B2 | 1/2015 | Eberle et al. | |
| 9,101,278 B2 | 8/2015 | Fischell et al. | |
| 9,167,747 B1 | 10/2015 | Andros et al. | |
| 9,307,920 B2 | 4/2016 | Mahajan et al. | |
| 9,314,210 B2 | 4/2016 | Li | |
| 9,339,662 B2 | 5/2016 | Allavatam et al. | |
| 9,381,370 B2 | 7/2016 | Gunderson | |
| 9,468,766 B2 | 10/2016 | Sheldon et al. | |
| 9,675,261 B2 | 6/2017 | Cao et al. | |
| 9,682,238 B2 | 6/2017 | Zhang et al. | |
| 9,724,007 B2 | 8/2017 | Cole | |
| 9,962,100 B2 | 5/2018 | Allavatam et al. | |
| 9,993,653 B2 | 6/2018 | Bardy et al. | |
| 9,999,368 B2 | 6/2018 | Perschbacher et al. | |
| 10,004,418 B2 | 6/2018 | Cao et al. | |
| 10,183,171 B2 | 1/2019 | Ostroff et al. | |
| 10,576,288 B2 | 3/2020 | Cao et al. | |
| 10,582,870 B2 | 3/2020 | Allavatam et al. | |
| 10,702,180 B2 | 7/2020 | Perschbacher et al. | |
| 10,709,379 B2 | 7/2020 | Warren et al. | |
| 11,559,242 B2 * | 1/2023 | Badie .................... | A61B 5/361 |
| 11,647,940 B2 * | 5/2023 | Badie .................... | A61B 5/361 600/510 |
| 2005/0080347 A1 | 4/2005 | Sheth et al. | |
| 2006/0247548 A1 * | 11/2006 | Sarkar .................... | A61B 5/363 600/515 |
| 2008/0161870 A1 | 7/2008 | Gunderson | |
| 2011/0270333 A1 | 11/2011 | Stadler et al. | |
| 2016/0129263 A1 | 5/2016 | Demmer et al. | |
| 2021/0236041 A1 * | 8/2021 | Badie .................... | A61B 5/7275 |
| 2021/0338136 A1 * | 11/2021 | Badie .................... | A61B 5/352 |
| 2021/0369176 A1 * | 12/2021 | Badie .................... | G16H 50/20 |
| 2022/0104774 A1 * | 4/2022 | Qu ........................ | A61B 5/7264 |

FOREIGN PATENT DOCUMENTS

| | | |
|---|---|---|
| EP | 2079520 B1 | 11/2013 |
| EP | 1877137 B1 | 10/2014 |
| EP | 2967402 B1 | 1/2016 |
| EP | 2364107 B1 | 9/2016 |
| EP | 1219237 B1 | 2/2017 |
| EP | 3247453 B1 | 11/2017 |
| EP | 2895063 B1 | 1/2019 |
| EP | 3422934 B1 | 1/2019 |
| EP | 3432774 B1 | 1/2019 |
| EP | 3592419 B1 | 1/2020 |
| EP | 2741662 B1 | 3/2021 |
| JP | 2016137038 A | 8/2016 |
| WO | WO03/105020 A2 | 12/2003 |

OTHER PUBLICATIONS

Chinese Office Action dated Nov. 14, 2023, Chinese Patent Application No. 202110612567.4.
English Abstract of Chinese Publication No. CN105326477 published Feb. 17, 2016.
Office Action dated Apr. 18, 2024, Chinese Patent Application No. 202110612567.4.
Communication under Rule 71(3) EPC dated Mar. 29, 2023, European Patent Application No. 21175590.5.
Extended European Search Report dated Oct. 21, 2019, European Patent Application No. 21175590.5-1122.
Response to Office Action dated Feb. 27, 2024, Chinese Patent Application No. 202110612567.4.
Response to Office Action dated Jun. 17, 2024, Chinese Patent Application no. 202110612567.4.
English translation of amended claims filed in Response to Office Action dated Jun. 17, 2024, Chinese Patent Application No. 202110612567.4.

* cited by examiner

METHODS, DEVICES AND SYSTEMS FOR IDENTIFYING FALSE R-R INTERVALS AND FALSE ARRHYTHMIA DETECTIONS DUE TO R-WAVE UNDERSENSING OR INTERMITTENT AV CONDUCTION BLOCK

PRIORITY CLAIM

The present application claims priority to U.S. Provisional Patent application No. 63/033,815, filed Jun. 2, 2020, and U.S. Provisional Patent application No. 63/043,932, filed Jun. 25, 2020, each of which is incorporated herein by reference.

FIELD OF TECHNOLOGY

Embodiments described herein relate to techniques for identifying false R-R intervals, as well as techniques for identifying false arrhythmia detections, resulting from R-wave undersensing or intermittent AV conduction block. Embodiments described herein can also be used to improve initial arrhythmia detections and to detect potential AV conduction block.

BACKGROUND

Various types of implantable medical devices (IMDs) are used to monitor for cardiac arrhythmias. Some types of IMDs, such as implantable cardiac pacemakers and implantable cardiac defibrillators (ICDs), are capable of providing appropriate therapy in response to detected cardiac arrhythmias. Other types of IMDs, such as insertable cardiac monitors (ICMs), are used for diagnostic purposes. ICMs have been increasingly used to diagnose cardiac arrhythmias, particularly atrial fibrillation (AF).

Atrial Fibrillation (AF) is a very common type of supraventricular tachycardia (SVT) which leads to approximately one fifth of all strokes, and is the leading risk factor for ischemic stroke. However, AF is often asymptomatic and intermittent, which typically results in appropriate diagnosis and/or treatment not occurring in a timely manner. To overcome this, many cardiac devices, such as ICMs, now monitor for AF by obtaining an electrogram (EGM) signal and measuring R-R interval variability based on the EGM signal. For example, an ICM or other IMD can compare measures of R-R interval variability to a variability threshold, to automatically detect AF when the variability threshold is exceeded. Indeed, ICMs predominantly identify AF by quantifying the variability in R-R intervals (i.e., by quantifying the variability in the timing of ventricular contractions). Episodes of other types of arrhythmias can additionally or alternatively be detected based on detected R-R intervals, such as, but not limited to, tachycardia, bradycardia, cardiac pause (also known as asystole), and ventricular fibrillation (VF).

When an IMD detects an episode of AF, or some other type of arrhythmic episode, information about the arrhythmic episode may be recorded and a corresponding EGM segment (and/or other information) can be transmitted from the IMD to a patient care network for clinician review. False positive arrhythmic detections (e.g., false positive AF detections) are highly undesirable, as the burden of sorting through large numbers of clinically irrelevant arrhythmic episodes can be time consuming and costly.

In various IMDs, such as ICMs, clinicians are provided with the capability of programming an R-wave sensing threshold, to which samples of an EGM are compared to detect R-waves in the EGM. Clinicians tend to keep the R-wave sensing threshold at its nominal value if the IMD demonstrates adequate R-wave amplitudes at implant and follow-up visits. However, depending on various factors, such as the IMD implant angle relative to the heart, R-wave amplitude may dynamically change and can occasionally be too small to detect. This can lead to R-wave undersensing, unless clinicians lower the programmable R-wave sensing threshold to correct this. In other cases, P-wave and/or T-wave oversensing resulting from P-wave and/or T-wave amplitudes exceeding the R-wave sensing threshold may lead clinicians to raise the programmable R-wave sensing threshold, which may also result in R-wave undersensing. Such R-wave undersensing, P-wave oversensing and/or T-wave oversensing can lead to false positive detections of arrhythmias, such as AF. Another reason for false positive detections of arrhythmias, such as AF, is intermittent atrioventricular (AV) conduction block, which results in R-waves intermittently not being present. Although the R-R intervals sensed by the IMD may be correct during an intermittent AV conduction block, this phenomenon may also result in R-R interval variability that leads to false positive detections of AF or VF. Accordingly, there is a still a need for improved arrhythmia detection specificity, such as, but not limited to, AF and VF detection specificity.

SUMMARY

Described herein are methods, devices, and systems for identifying false R-R intervals, and false arrhythmia detections, resulting from R-wave undersensing or intermittent AV conduction block. Embodiments described herein can also be used to improve initial arrhythmia detections and to detect potential AV conduction block. In accordance with certain embodiments, a method comprises: obtaining information for at least three R-R intervals, wherein each of the R-R intervals has a respective duration, and each of the R-R intervals may be a true R-R interval or a false R-R interval; and classifying one of the R-R intervals as being a false R-R interval, in response to both (i) determining that the duration of the one of the R-R intervals is greater than a first specified threshold, and (ii) determining that the duration of the one of the R-R intervals is within a second specified threshold of being an integer multiple of at least X of the other R-R intervals for which information is obtained, wherein the integer multiple is at least 2, and wherein X is a specified integer that is 1 or greater. Where such a method is used to identify one or more false R-R intervals, it is presumed the false R-R intervals are associated with R-wave undersensing or AV conduction block.

In accordance with certain embodiments, the other R-R intervals, which are used in the (ii) determining that the duration of the one of the R-R intervals is within the second specified threshold of being an integer multiple of at least X of the other R-R intervals, comprise at least N neighboring R-R intervals, wherein N is a specified integer that is 6 or greater, and N is greater than X. In accordance with certain such embodiments, the at least N neighboring R-R intervals includes at least M immediately preceding R-R intervals and at least M immediately following R-R intervals, where M is a specified integer that is 3 or greater.

In accordance with certain embodiments, the (ii) determining that the duration of the R-R interval is within the second specified threshold of being an integer multiple of a duration of at least X neighboring R-R interval(s), comprises for each neighboring R-R interval of the at least X neighboring R-R interval(s): determining a ratio of the duration of the R-R interval to the duration of the neighboring R-R interval; rounding the ratio to its closest integer to produce a rounded ratio; determining that the rounded ratio has a value of at least 2; determining an indication of a difference between the R-R interval and the rounded ratio that has the value of at least 2; and determining that the indication of the difference between the R-R interval and the rounded ratio is within a difference threshold that comprises the second specified threshold.

In accordance with certain embodiments, the first specified threshold is 600 ms, and the (i) determining that the duration of the one of the R-R intervals is greater than the first specified threshold comprises determining that the duration of the one of the R-R intervals is greater than 600 ms. In accordance with certain embodiments, the second specified threshold is a percent, such as 10%, but is not limited thereto.

In accordance with certain embodiments, the at least three R-R intervals (for which information is obtained) are R-R intervals included in a window leading up to a detection of a potential arrhythmic episode (e.g., a potential AF episode); and the method further comprises using results of the classifying to determine whether the potential arrhythmic episode (e.g., the potential AF episode) is a false positive. In accordance with certain embodiments, the using results of the classifying to determine whether the potential arrhythmic episode is a false positive comprises: determining whether at least a threshold amount of the R-R intervals, within the window leading up to the detection of the potential arrhythmic episode, are classified as being a false R-R interval (associated with R-wave undersensing or AV conduction block); and the using results of the classifying to determine whether the potential arrhythmic episode is a false positive detection is also based on determining that at least the threshold amount of the R-R intervals, within the window leading up to the detection of the potential AF episode, are classified as being a false R-R interval. In accordance with certain embodiments, where the potential arrhythmic episode is a potential AF or VF episode, then using results of the classifying to determine whether the potential AF or VF episode is a false positive also comprises: removing, from the window leading up to the detection of the potential AF or VF episode, all of the R-R intervals that are classified as being a false R-R interval (associated with R-wave undersensing or AV conduction) to thereby produce a corrected window; determining for the R-R intervals remaining in the window, after the removing, a median indicator of an interval-to-interval difference; and determining that the potential AF or VF episode is a false positive based on the median indicator of an interval-to-interval difference being less than a further specified threshold.

In accordance with certain embodiments, the method comprises grouping the R-R intervals into two or more groups based on the durations of the R-R intervals, such that R-R intervals that are within a third specified threshold of one another are grouped into a same one of the groups; and classifying one of the groups that includes a greatest number of R-R intervals as a dominant group. In such embodiments, the other R-R intervals, which are used in the (ii) determining that the duration of the one of the R-R intervals is within the second specified threshold of being an integer multiple of at least X of the other R-R intervals, comprise R-R intervals within the dominant group. In accordance with certain such embodiments, the grouping results in a histogram including a plurality of bins, each of which corresponds to one of the groups that include R-R intervals that are within the third specified threshold (e.g., 15%) of one another; and the classifying one of the groups as the dominant group is performed by identifying the group corresponding to the bin of the histogram that has the greatest number of R-R intervals therein.

Certain embodiments of the present technology are directed to a device comprising one or more electrodes, a sensing circuit, and at least one of a processor or controller. The sensing circuit is coupled to the one or more electrodes and configured to obtain a signal indicative of cardiac electrical activity, such as an EGM or electrocardiogram (ECG). The at least one of the processor or controller is/are configured to: determine, based on the signal indicative of cardiac electrical activity, information for at least three R-R intervals included in the signal, wherein each of the R-R intervals has a respective duration, and each of the R-R intervals may be a true R-R interval or a false R-R interval; determine whether the duration of one of the R-R intervals is greater than a first specified threshold; determine whether the duration of the one of the R-R intervals is within a second specified threshold of being an integer multiple of at least X of the other R-R intervals for which information is obtained, wherein the integer multiple is at least 2, and wherein X is a specified integer that is 1 or greater; and determine whether to classify the one of the R-R intervals as being a false R-R interval, based on whether the duration of the one of the R-R intervals is determined to be greater than the first specified threshold, and based on whether the duration of the one of the R-R intervals is determined to be within the second specified threshold of being an integer multiple of at least X of the other R-R intervals for which information is obtained.

In accordance with certain embodiments, the other R-R intervals, which are used to determine whether the duration of the one of the R-R intervals is within the second specified threshold of being an integer multiple of at least X of the other R-R intervals, comprise at least N neighboring R-R intervals, wherein N is a specified integer that is 6 or greater, and N is greater than X. In accordance with certain such embodiments, the at least N neighboring R-R intervals includes at least M immediately preceding R-R intervals and at least M immediately following R-R intervals, where M is a specified integer that is 3 or greater.

In accordance with certain embodiments, in order to determine whether the duration of the R-R interval is within the second specified threshold of being an integer multiple of a duration of at least X neighboring R-R interval(s), the least one of the processor or controller is/are configured to perform the following for each neighboring R-R interval of the at least X neighboring R-R interval(s): determine a ratio of the duration of the R-R interval to the duration of the neighboring R-R interval; round the ratio to its closest integer to produce a rounded ratio; determine whether the rounded ratio has a value of at least 2; if the rounded ratio has a value of at least 2, determine an indication of a difference between the R-R interval and the rounded ratio that has the value of at least 2; and determine whether the indication of the difference between the R-R interval and the rounded ratio is within a difference threshold that comprises the second specified threshold.

In accordance with certain embodiments, the at least three R-R intervals (for which information is obtained) are included in a window leading up to a detection of a potential arrhythmic episode, and the at least one of the processor or controller is/are configured to determine whether the potential arrhythmic episode is a false positive based on whether at least a threshold amount of the R-R intervals, within the window leading up to the detection of the potential arrhythmic episode, are classified as being a false R-R interval. In accordance with certain such embodiments, the at least one of the processor or controller is/are configured to: remove, from the window leading up to the detection of a potential AF or VF episode, all of the R-R intervals that are classified as being a false R-R interval to thereby produce a corrected window; determine for the R-R intervals remaining in the window, after the removing, a median indicator of an interval-to-interval difference; and determine that the potential AF or VF episode is a false positive also based on the median indicator of the interval-to-interval difference being less than a further specified threshold.

In accordance with certain embodiments, the at least one of the processor or controller is/are configured to: group the R-R intervals into two or more groups based on the durations of the R-R intervals, such that R-R intervals that are within a third specified threshold of one another are grouped into a same one of the groups; and classify one of the groups that includes a greatest number of R-R intervals as a dominant group; wherein the other R-R intervals, which are used to determine whether the duration of the one of the R-R intervals is within the second specified threshold of being an integer multiple of at least X of the other R-R intervals, comprise R-R intervals within the dominant group.

In accordance with certain embodiments, the device comprises an implantable medical device (IMD) including a telemetry circuit configured to enable the IMD to communicate with an external device, and memory configured to store data corresponding to one or more arrhythmic episodes detected by the IMD. In certain such embodiments, the at least one of a processor or controller is/are further configured to at least one of: prevent transmission by the telemetry circuit, to an external device that is communicatively coupled to a patient care network, of data corresponding to a potential arrhythmic episode that is detected by the IMD but is thereafter determined by the IMD as being a false positive detection; allow overwriting in the memory of data corresponding to a potential arrhythmic episode that was detected by the IMD but is thereafter determined by the IMD as being a false positive detection; or prevent storing in the memory of data corresponding to a potential arrhythmic episode that is detected by the IMD but is thereafter determined by the IMD as being a false positive detection.

Certain embodiments of the present technology are directed to a method for determining whether to classify a detection of a potential arrhythmic episode as a false positive detection. Such a method can include obtaining information for at least three R-R intervals including in a window leading up to the detection of the potential arrhythmic episode, wherein each of the R-R intervals has a respective duration, and each of the R-R intervals may be a true R-R interval or a false R-R interval. The method can also include for each R-R interval of a plurality of the R-R intervals included in the window, classifying the R-R interval as being a false R-R interval associated with R-wave undersensing or AV conduction block, in response to both: determining that the duration of the R-R interval is greater than a first specified threshold; and determining that the duration of the R-R interval is within a second specified threshold of being an integer multiple of at least X of the other R-R intervals for which information is obtained, wherein the integer multiple is at least 2, and wherein X is a specified integer that is 1 or greater. The method can further include classifying the detection of a potential AF or VF episode as a false positive detection, in response to both: at least a first threshold amount of the R-R intervals, within the window leading up to the detection of the potential AF or VF episode, being classified as being a false R-R interval associated with R-wave undersensing or AV conduction; and a median indicator of an interval-to-interval difference, of R-R intervals within the window that are not classified as being a false R-wave associated with R-wave undersensing or AV conduction block, being greater than a further specified threshold.

Certain embodiments of the present technology are directed to a device comprising one or more electrodes, a sensing circuit coupled to the one or more electrodes and configured to obtain a signal indicative of cardiac electrical activity, and at least one of a processor or controller. The processor and/or controller is/are configured to determine, based on the signal indicative of cardiac electrical activity, information for R-R intervals including in a window leading up to the detection of the potential AF or VF episode, wherein each of the R-R intervals has a respective duration, and each of the R-R intervals may be a true R-R interval or a false R-R interval. The processor and/or controller is/are also configured to, for each R-R interval of a plurality of the R-R intervals included in the window, classify the R-R interval as being a false R-R interval associated with R-wave undersensing or AV conduction block, in response to both: the duration of the R-R interval being greater than a first specified threshold, and the duration of the R-R interval being within a second specified threshold of being an integer multiple of at least X of the other R-R intervals for which information is obtained, wherein the integer multiple is at least 2, and wherein X is a specified integer that is 1 or greater. The processor and/or controller is also configured to classify the detection of the potential AF or VF episode as a false positive detection, in response to both: at least a first threshold amount of the R-R intervals, within the window leading up to the detection of the potential AF or VF episode, being classified as being a false R-wave associated with R-wave undersensing or AV conduction block, and a median indicator of an interval-to-interval difference, of R-R intervals within the window that are not classified as being a false R-wave associated with R-wave undersensing or AV conduction block, being greater than a further specified threshold. In accordance with certain embodiments, the device comprises an IMD including a telemetry circuit configured to enable the IMD to communicate with an external device, and memory configured to store data corresponding to one or more arrhythmic episodes detected by the IMD.

In accordance with certain embodiments, the processor and/or controller of the IMD is/are further configured to at least one of: prevent transmission by the telemetry circuit, to an external device that is communicatively coupled to a patient care network, of data corresponding to a potential AF or VF episode that is detected by the IMD but is thereafter determined by the IMD as being a false positive detection; allow overwriting in the memory of data corresponding to a potential AF or VF episode that was detected by the IMD but is thereafter determined by the IMD as being a false positive detection; or prevent storing in the memory of data corresponding to a potential AF or VF episode that is detected by the IMD but is thereafter determined by the IMD as being a false positive detection.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

DETAILED DESCRIPTION

Figure 1:
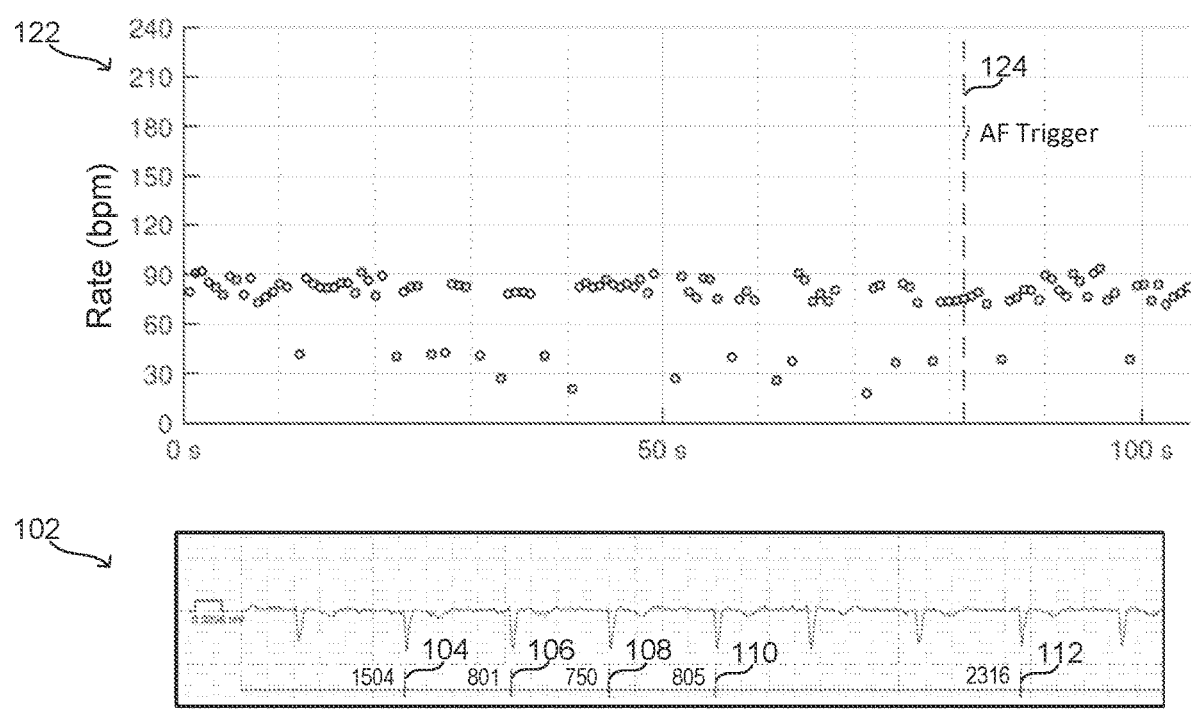
FIG. 1 includes a portion of an EGM segment that resulted in an AF detection due to under-sensed R-waves, and also includes a corresponding graph of heart rate (HR) versus time.

It is well known that each cardiac cycle represented within an EGM or ECG typically includes a P-wave, followed by a QRS complex, followed by a T-wave, with the QRS complex including Q-, R-, and S-waves. The P-wave is caused by depolarization of the atria. This is followed by atrial contraction, which is indicated by a slight rise in atrial pressure contributing to further filling of the ventricle. Following atrial contraction is ventricular depolarization, as indicated by the QRS complex, with ventricular depolarization initiating contraction of the ventricles resulting in a rise in ventricular pressure until it exceeds the pulmonary and aortic diastolic pressures to result in forward flow as the blood is ejected from the ventricles. Ventricular repolarization occurs thereafter, as indicated by the T-wave and this is associated with the onset of ventricular relaxation in which forward flow stops, the pressure in the ventricle falls below that in the atria at which time the mitral and tricuspid valves open to begin to passively fill the ventricle during diastole. The terms EGM, EGM signal, and EGM waveform are used interchangeably herein. Similarly, the terms ECG, ECG signal, and ECG waveform are used interchangeably herein. Both ECG and EGM signals are signals indicative of electrical activity of a patient's heart.

The R-wave is typically the largest wave in the QRS complex, and it often identified by comparing samples of an EGM or ECG to an R-wave threshold. Various measurements can be obtained based on the EGM or ECG waveform, including measurements of R-R intervals, where an R-R interval is the duration between a pair of consecutive R-waves. As noted above, in the Background, a common technique for detecting AF is based on measures of R-R interval variability. However, for various reasons, including an implant angle of an IMD relative to the heart, the dynamically changing R-wave amplitude may occasionally be too small to detect leading to R-wave undersensing, unless clinicians lower the programmable R-wave sensing threshold to correct this. In other cases, P-wave and/or T-wave oversensing resulting from P-wave and/or T-wave amplitudes exceeding the R-wave sensing threshold may lead clinicians to raise the programmable R-wave sensing threshold, which may also result in R-waves undersensing. Where T-waves and/or P-waves are falsely identified as R-waves, false R-R intervals can be identified which have a high variability, leading to false detections of AF. In other words, over-sensed P-waves and/or over-sensed T-waves can lead to false positive AF detections. An over-sensed P-wave, as the term is used herein, refers to a P-wave that is falsely identified as an R-wave. Similarly, an over-sensed T-wave, as the term is used herein, refers to a T-wave that is falsely identified as an R-wave. An under-sensed R-wave, as the term is used herein, refers to an R-wave that is not detected. An over-sensed R-wave, as the term is used herein, refers to a feature (e.g., a P-wave or a T-wave) of an EGM or ECG that is falsely identified as an R-wave.

R-wave undersensing can lead to false positive detections of arrhythmic episodes, such as AF. As also noted above, another reason for false positive detections of arrhythmic episodes is intermittent AV conduction block, which can result in R-R interval variability measurements that results in false positive detections of arrhythmias, even if the R-R intervals sensed by the IMD are correctly sensed during the intermittent AV conduction block. Interestingly, both R-wave undersensing and intermittent AV conduction block result in R-R interval measurements that are close to integer-multiples of neighboring R-R intervals. Certain embodiments of the present technology described herein relate to techniques for identifying instances of R-wave undersensing or AV conduction block using only the sensed R-R intervals. An IMD can use such a technique to reject false positive arrhythmia (e.g., AF) detections before they are transmitted to a clinician, consequently improving arrhythmia detection specificity and reducing downstream clinical resources. More specifically, certain embodiments rely on the fact that one under-sensed or blocked R-wave effectively doubles the perceived R-R interval. Likewise, two successively under-sensed or blocked R-waves triple the R-R interval, and so on. Thus, the ratio of each R-R interval to its neighboring R-R intervals can be used to identify potential instances of R-wave undersensing or AV conduction block. In accordance with certain embodiments, if the ratio is sufficiently close to an integer (e.g. 2.05, 3.96, etc. . . . ) and the R-R interval is sufficiently long (e.g., greater than 0.6 seconds, and thus, corresponding to a heart rate of less than 100 bpm), then the R-R interval is likely the result of one or more under-sensed and/or blocked R-waves. Explain another way, the duration of an R-R interval relative to the durations of its neighboring R-R intervals can be used to identify potential instances of R-wave undersensing or AV conduction block. More specifically, where the duration of an R-R interval is sufficiently close to being an integer multiple (e.g. 2.05, 3.96, etc. . . . ) of the durations of its neighboring R-R intervals and the R-R interval is sufficiently long (e.g., greater than 0.6 seconds, and thus, corresponding to a heart rate of less than 100 bpm), then the R-R interval is likely the result of one or more under-sensed and/or blocked R-waves. Because these aforementioned criteria may still be met during an actual arrhythmia (e.g., actual AF), each potential arrhythmia detection should be verified (i.e., reevaluated) after removing or otherwise ignoring the potentially under-sensed/blocked R-R intervals.

Certain embodiments of the present technology relate to methods and devices that use sensed R-R intervals to determine whether R-wave undersensing and/or AV conduction block has occurred, and more generally, to distinguish true R-R intervals from false R-R intervals. These embodiments can beneficially be used, for example, to prevent or reject false positive arrhythmia detections (e.g., false positive AF detections) before they are transmitted to a clinician, consequently improving arrhythmia detection specificity and reducing downstream clinical resources. A true R-R interval, as the term is used herein, refers to an actual R-R interval corresponding to a period of non-AV condition block. A false R-R interval, as the term is used herein, refers to an interval that is mistakenly identified as an R-R interval, but is not an actual R-R interval. A false R-R interval may occur because of R-wave undersensing, e.g., if R-waves are correctly identified in portions of an EGM corresponding to an nth cardiac cycle and an (n+2)th cardiac cycle, but the R-wave is not identified due to R-wave undersensing in the (n+1)th cardiac cycle, leading to an R-R interval measurement being about double the true R-R interval. A false R-R interval may alternatively or additionally occur because of AV conduction block, e.g., if R-waves are present and correctly identified in portions of an EGM corresponding to an nth cardiac cycle and an (n+2)th cardiac cycle, but the R-wave is not present in the (n+1)th cardiac cycle because of AV conduction block, leading to an R-R interval measurement being about double the true R-R interval.

Other example types of intervals that may be mistakenly identified as an R-R interval, and thus are examples of false R-R intervals, include, but are not limited to, P-R intervals, R-T intervals, P-T intervals, and T-P intervals. A P-R interval can be mistakenly identified as an R-R interval where a P-wave is over-sensed. An R-T interval can be mistakenly identified as R-R interval where a T-wave is over-sensed. A P-T interval or a T-P interval can be mistakenly identified as an R-R interval where T- and P-waves are over-sensed and an R-wave is under-sensed. These types of false R-R intervals can also be referred to as over-sensed R-R intervals. Embodiments of the present technology described herein do not specifically address over-sensed R-R intervals, but can be used together with techniques to do address these other types of false R-R intervals to further increase arrhythmia detection specificity, and more generally, increase arrhythmia detection accuracy.

Certain embodiments of the present technology described herein rely on the phenomenon that R-wave undersensing or AV conduction block effectively causes a measured R-R interval to be substantially similar to an integer multiple (e.g., 2× or 3×) of a normal R-R interval, which can also be referred to as a true R-R interval or an actual R-R interval. Thus, certain embodiments of the present technology identify intervals that are similar to an integer multiple of either the previous three (or some other number of) intervals or the next three (or some other number of) intervals, which are the real R-R intervals and do not correspond to R-wave undersensing or AV conduction block. Further analysis (e.g., arrhythmia detection analysis) can then proceed using only the remaining R-R intervals.

In accordance with certain embodiments, a list of sensed R-R intervals is obtained for a recorded EGM clip, which can also be referred to as a segment of an EGM, or an EGM segment. Because this list of R-R intervals may actually include one or more false R-R intervals, e.g., due to R-wave undersensing and/or intermittent AV conduction block, unless specifically referred to as being a "true R-R interval", any interval referred to herein generally as an R-R interval may be a false R-R interval or a true R-R interval. It is also noted that the term potential R-R interval refers to an R-R interval that may be a false R-R interval or a true R-R interval. Further, it is noted that while a large portion of the following description and the patient example discussed below describes R-wave undersensing, the same principles also apply to intermittent AV conduction block.

An example of R-wave undersensing is shown if FIG. 1, taken directly from an EGM clip file of a patient having an implanted Confirm RX™ ICM. Although this specific example corresponds to an R-R interval pattern that resulted from R-wave undersensing, the same R-R interval pattern may be the result of intermitted AV conduction block, and the same principles would apply. At the bottom of FIG. 1 is shown a portion of an EGM segment 102 that resulted in an AF detection due to under-sensed R-waves. At the top of FIG. 1 is shown a graph or plot 122 that includes heart rate (HR) in beats per minute (bpm) along the vertical axis, and time in seconds (s) along the horizontal axis. The dashed vertical line 124 corresponds to an AF detection occurring at a point in time corresponding to ~82 seconds, and thus, the vertical line 124 is also marked AF Trigger. Because the AF detection represented by the dashed vertical line 124 may actually be a false AF detection, it can also be referred to more specifically as a potential AF detection, wherein the potential AF detection may or may not be a true AF detection. The potential AF detection may have been detected, e.g., if a measure of R-R interval variability exceeds a corresponding threshold, but is not limited thereto. Example techniques for detecting an AF episode, or more specifically, a potential AF episode, are described in U.S. Pat. No. 8,121,675 to Shaquer et al., titled "Device and Method for Detecting Atrial Fibrillation," which is incorporated herein by reference. The use of other techniques for detecting potential AF episodes, as well as other types of arrhythmias, are also possible and within the scope of the embodiments described herein.

Figure 2:
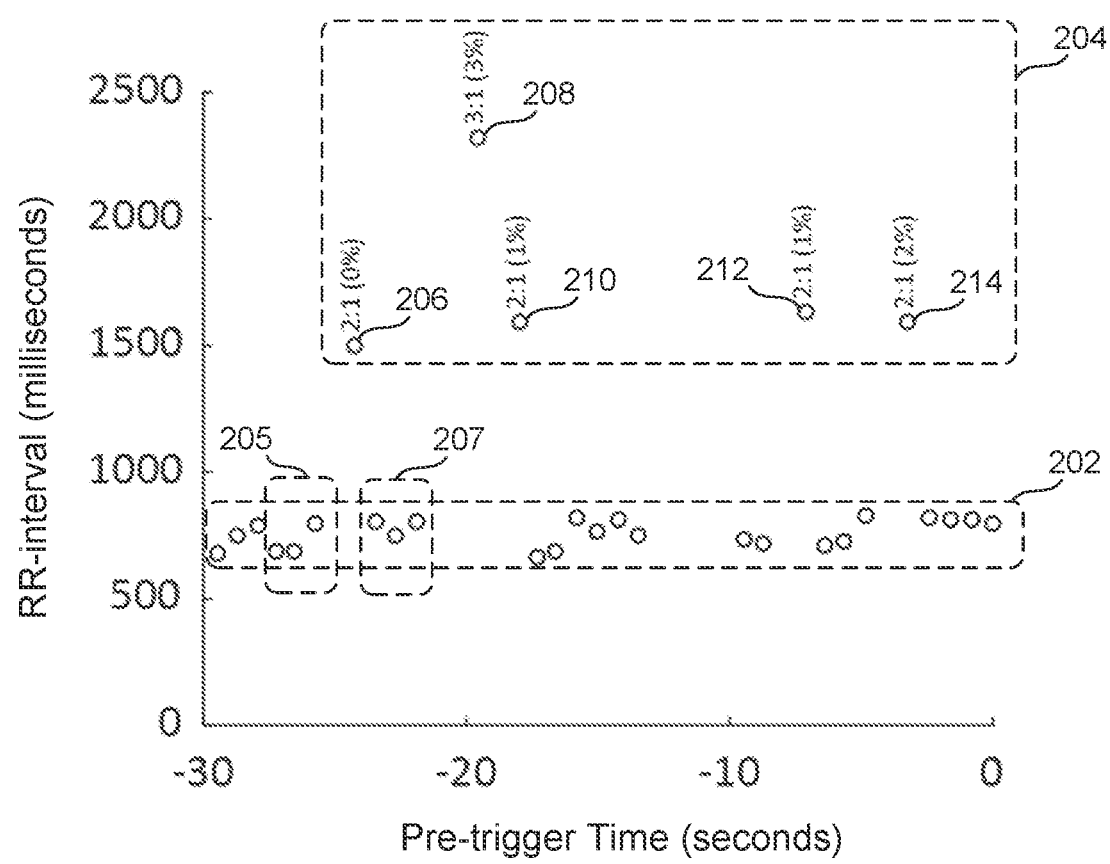
FIG. 2 includes a graph of R-R intervals for a window preceding the AF detection in FIG. 1, which R-R intervals correspond to the inverse of the heart rates shown in FIG. 1.

FIG. 2 illustrates a graph or plot of R-R intervals in milliseconds (ms) for a 30 second (s) window preceding the AF trigger 124 in FIG. 1, which R-R intervals correspond to the inverse of the heart rates that were shown in FIG. 1. In FIG. 2, the circles within the dashed outline 202 correspond to R-R intervals that are true R-R intervals, and the circles within the dashed outline 204 correspond to R-R intervals associated with under-sensed R-waves (with the maximum ratio and % difference relative to neighboring R-R intervals indicated next to each circle within the dashed outline 204). Since the R-R intervals within the dashed outline 204 are not true R-R intervals, they can be referred to as false R-R intervals.

Figure 3:
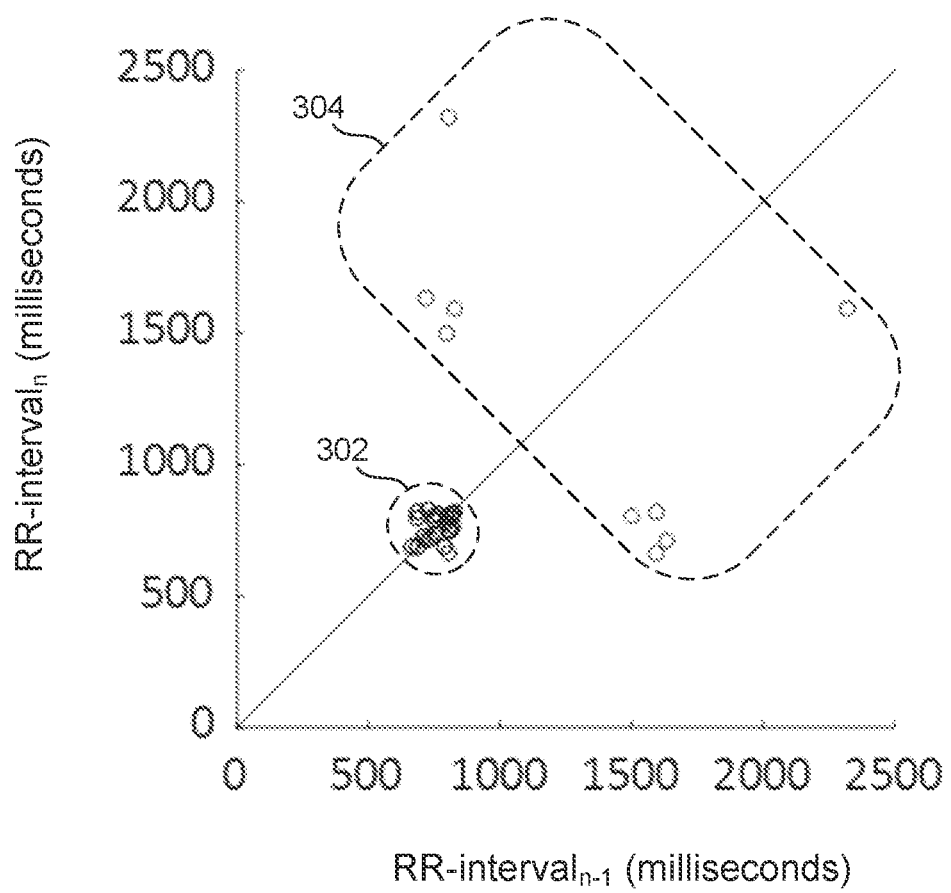
FIG. 3 includes a Poincare plot that illustrates the relationship between each R-R interval in the EGM segment shown in FIG. 1 and its immediately following R-R interval, i.e., illustrates the relationship between successive R-R intervals.

The Poincare plot shown in FIG. 3 plots the relationship between each R-R interval in the EGM segment 102 and its immediately following R-R interval, i.e., illustrates the relationship between successive R-R intervals. The circles within the dashed outline 302 correspond to true R-R intervals. The circles within the dashed outline 304 correspond to false R-R intervals that result from R-wave undersensing. Similar false R-R intervals may result for intermittent AV conduction block, instead of R-wave undersensing.

In accordance with certain embodiments, for each R-R interval in a window (e.g., a 30 second window) preceding the AF trigger (i.e., leading up to the detection of a potential AF episode), a ratio ("r") is calculated relative to each of a number of neighboring R-R intervals (e.g., the immediately preceding three intervals and immediately following three intervals). In specific embodiments, the analysis skips the first three (or some other number of) R-R intervals and last three (or some other number of) R-R intervals in the 30 second window, since the R-R intervals near the start and the end of the window have minimal neighbors to one side. All the ratios that round to less than 2 are eliminated.

Next, after the R-R intervals having a rounded ratio of less than 2 are eliminated, an indicator of a difference between each remaining analyzed R-R interval and its neighboring R-R intervals is determined. In certain embodiments, the indicator of the difference between each analyzed R-R interval and its neighboring R-R intervals is a percent difference that is calculated using the following equation:

$$\% \text{ difference} = 100 \times |r - \text{round}(r)| / \text{round}(r)$$

where, r is the ratio of the analyzed R-R interval relative to a neighboring R-R interval, and round (r) is the calculated ratio rounded to the nearest integer.

The minimum percent difference (or more generally, the minimum indicator of the difference) for an analyzed R-R interval relative to all six (or some other number of) neighbors is then used to potentially flag the analyzed R-R interval as being associated with undersensing or AV conduction block. These rounded ratios and percent differences are listed next to each of the circles within the dashed outline 204 in FIG. 2. More specifically, for the circle labeled 206 (at approximately 25 seconds prior to the AF trigger) the rounded ratio is 2:1 and the percentage difference is 0%; for the circle labeled 208 (at approximately 20 seconds prior to the AF trigger) the rounded ratio is 3:1 and the percentage difference is 3%; for the circle labeled 210 (at approximately 18 seconds prior to the AF trigger) the rounded ratio is 2:1 and the percentage difference is 1%; for the circle labeled 212 (at approximately 7 seconds prior to the AF trigger) the rounded ratio is 2:1 and the percentage difference is 1%; and for the circle labeled 214 (at approximately 4 seconds prior to the AF trigger) the rounded ratio is 2:1 and the percentage difference is 2%.

Referring specifically to the circle labeled 206 (at approximately 25 seconds prior to the AF trigger), the under-sensed R-R interval has a duration (aka value) of 1500 milliseconds (ms). The durations (aka values) of the three neighboring R-R intervals immediately preceding the 1500 ms under-sensed R-R interval (represented by the three circles within the dashed outline labeled 205) are 700 ms, 700 ms, and 750 ms. The durations of three neighboring R-R intervals immediately following the 1500 ms under-sensed R-R interval (represented by the circles within the dashed outline labeled 207) are 760 ms, 740 ms, and 750 ms. The ratios of the under-sensed R-R interval (having the value of 1500 ms) relative to the three neighboring R-R intervals on either side are as follows: [1500/700, 1500/700, 1500/750, 1500/760, 1500/740, 1500/750]=[2.14, 2.14, 2.00, 1.97, 2.03, 2.00]. These correspond to % differences of: [7%, 7%, 0%, 1.5%, 1.5%, 0%]. The minimum % difference of 0% indicates that the current interval (1500 ms) is "close to" an integer multiple of a neighboring R-R interval (in this case, a 0% difference from 2× a neighboring R-R interval).

In accordance with certain embodiments, two criteria are ultimately applied in order to determine whether an R-R interval being analyzed (aka an analyzed R-R interval) should be classified as being a false R-R interval associated with R-wave undersensing or AV conduction block (which can be collectively referred to as R-wave undersensing/block), and thus, can be more generally classified as a false R-R interval.

One criteria is that the minimum percent difference of the ratios relative to all six (or some other number) of its neighbors is less than a specified difference threshold, e.g., less than 10%. This criterion ensures that the interval in question is reasonably close to an integer multiple of at least one of its neighboring R-R intervals, where the integer multiple is at least 2. Note that the minimum percent difference threshold may also be programmable depending on the clinical need. For example, it may be specified as less than 10% if AF sensitivity is important, but may alternatively be specified as greater than 10% (e.g., 15%) if a reduction in false positive AF detections (aka AF specificity) is preferred.

Another criteria is that the interval value is greater than a specified duration threshold, e.g., greater than 600 ms (i.e., corresponding to a HR of less than 100 bpm). This criterion ensures that P-wave or T-wave oversensing midway between an R-R interval does not result in a true R-R interval being flagged as a false R-R interval for being twice the duration of a neighboring R-R interval.

Once the false R-R-intervals (due to R-wave undersensing and/or AV conduction block) within the 30 second window (leading up to the potential AF detection, or other type of potential arrhythmia detection) have been identified, there is a determination of what percent of the R-R intervals were identified as false R-R intervals (due to R-wave undersensing and/or AV conduction block). This false R-R interval percentage, which can also be referred to more specifically as the "undersensing/AV conduction block percent," quantifies the incidence of R-wave undersensing and/or AV conduction block within the window.

In addition, the identified false R-R intervals (due to R-wave undersensing and/or AV conduction block) are removed from the ordered list of R-R intervals (included in the window leading up to the potential AF detection) to thereby produced a corrected list of R-R intervals. Based on the corrected list of R-R intervals, a median interval-interval % difference is calculated (using the above described equation % difference=100×|r–round(r)|/round(r)) to thereby produce a "corrected interval variability."

Ultimately, the entire window is classified (aka flagged) as being a false positive AF detection (due to R-wave undersensing and/or AV conduction block) if the following criteria are met: (1) the "undersensing/AV conduction block percent" is greater than a specified false-detection threshold (e.g., >5%), which criterion ensures that a sufficient number of undersensing/AV conduction block-related false R-R intervals exist, such that they may have influenced AF detection; and (2) the "corrected interval variability" is less than a specified variability threshold (e.g., <5%). Note that, during actual AF, some intervals may still be labeled as false R-R intervals (due to R-wave undersensing and/or AV conduction block) if they randomly are similar to integer-multiples of neighboring R-R intervals. This second criterion is used to recognize when the rhythm is otherwise stable, after false R-R intervals (due to R-wave undersensing and/or AV conduction block) have been removed.

The example window leading up to the potential AF detection, described above with reference to FIGS. 1-3, was associated with an "undersensing/AV conduction block percent" of 20.0% and a "corrected interval variability" of 3.4%, thus satisfying the above criteria to be flagged as a false AF detection.

Additional details of the embodiments summarized above are described below with reference to the high level flow diagrams in FIGS. 4A and 4B, which can be collectively referred to as FIG. 4. More specifically, FIG. 4 is used to summarize certain methods of the present technology for improving R-R interval detection specificity, and arrhythmia episode (e.g., AF episode) detection specificity. Such a method may be triggered in response to a detection of a potential arrhythmic episode (e.g., a potential AF episode). In other words, the methods summarized with reference to the high level flow diagram in FIG. 4 can be used to identify false R-R intervals that are due to R-wave undersensing and/or AV conduction blow, as well as to detect false positive arrhythmia detections.

Figure 4A:
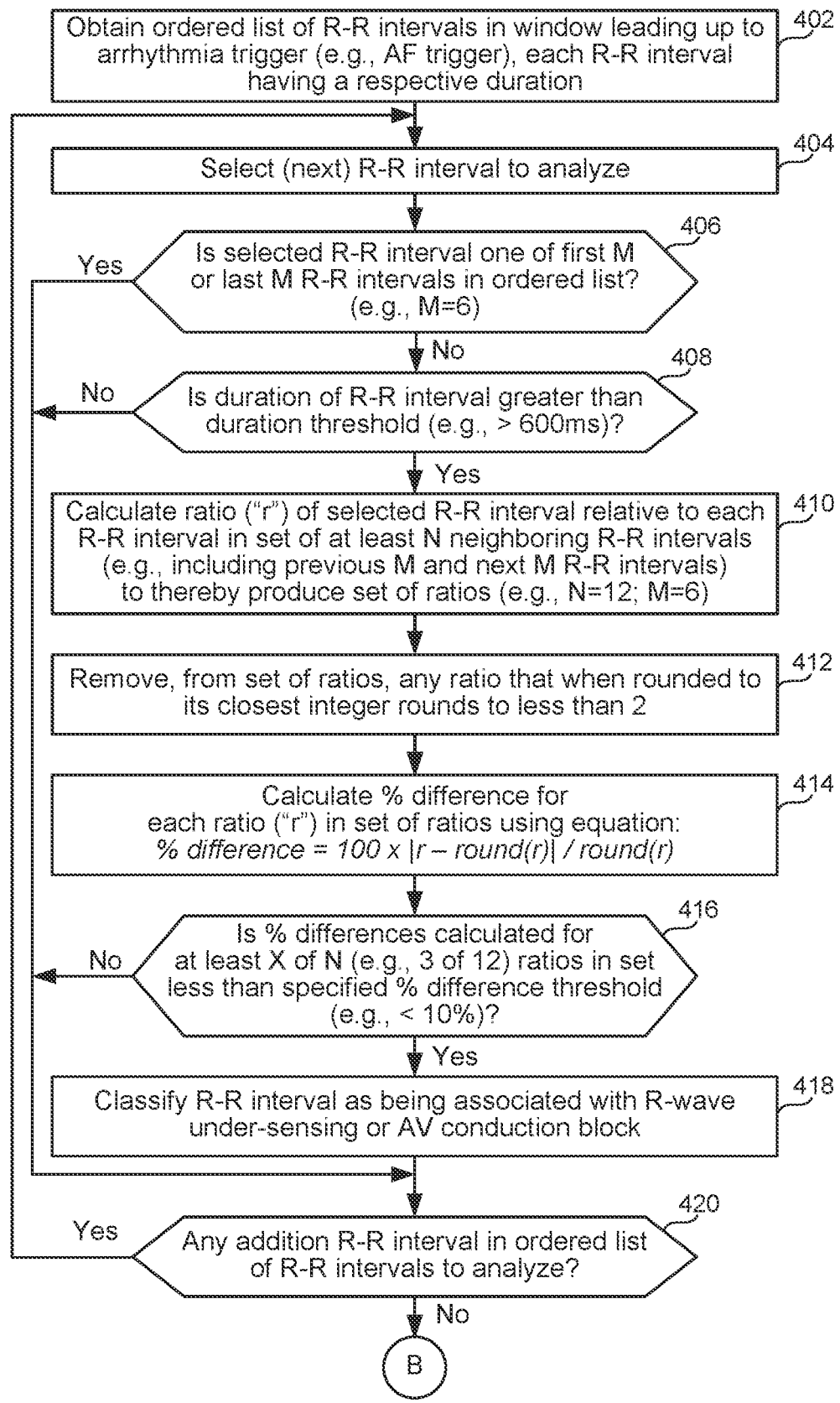
FIGS. 4A and 4B, which can be collectively referred to as FIG. 4, includes a high level flow diagram that is used to describe how true R-R intervals can be distinguished from false R-R intervals associated with R-wave undersensing or AV conduction block using embodiments of the present technology, and how the results of such an analysis can be used to determine whether to classify a detection of a potential AF episode as a false positive detection.

Referring to FIG. 4A, step 402 involves obtaining an ordered list of R-R intervals within a window leading up to a detection of a potential arrhythmic episode (e.g., a potential AF episode), wherein each of the R-R intervals has a respective duration. The ordered list of R-R intervals can be obtained, for example, by identifying R-waves within an EGM or ECG segment, and determining intervals between consecutive ones of the R-waves to thereby produce the ordered list of R-R intervals. Such R-waves can be identified within the EGM or ECG segment by comparing the EGM or ECG segment, or samples thereof, to an R-wave sensing threshold, and identifying R-waves when the R-wave sensing threshold is reached or exceeded. Other variations are also possible and within the scope of the embodiments described herein. For example, R-waves can alternatively or additionally be identified using R-wave or QRS complex morphology templates.

The ordered list of R-R intervals, obtained at step 402, would preferably include only true R-R intervals. However, due to R-wave undersensing and/or AV conduction block, the ordered list of intervals obtained at step 402 may also include one or more false R-R intervals. In other words, the ordered list of R-R intervals, included in the window leading up to the detection of the potential arrhythmic episode (aka an "arrhythmia trigger") (e.g., a potential AF episode (aka an "AF trigger")), in addition to including true R-R intervals, may also include one or more false R-R intervals that may be present, e.g., if R-waves are under-sensed (i.e., present but not detected) and/or if the patient experiences AV conduction block that results in one or more missing R-waves. In order to maximize the specificity of the methods summarized with reference to FIG. 4A, one or more techniques for identifying and removing or otherwise compensating for other types of false R-R intervals can be performed prior to step 402, as part of step 402, or between step 402 and the next step 404.

Step 404 involves selecting an R-R interval (from the ordered list of R-R intervals obtained at step 402) to analyze. The first time step 404 is performed (for an ordered list of intervals), the first R-R interval in the ordered list can be selected. The second time step 404 is performed (for the ordered list of intervals), the second R-R interval in the ordered list can be selected, and so on.

At step 406 there is a determination of whether the R-R interval (selected at step 404 for analysis) is the one of the first M or last M R-R intervals in the ordered list of intervals (e.g., M=3). If the selected interval is one of the first M or last M R-R intervals in the list (i.e., if the answer to the determination at step 406 is Yes), then flow goes to step 420 (thereby skipping steps 408 through 418). If the selected interval is not one of the first M or last M R-R intervals in the list (i.e., if the answer to the determination at step 406 is No), then flow goes to step 408.

At step 408 there is a determination of whether a duration of the R-R interval (selected at step 404 for analysis) is greater than a specified duration threshold, e.g., greater than 600 ms (i.e., corresponding to a HR of less than 100 bpm). As noted above, this criterion ensures that P-wave or T-wave oversensing midway between an R-R interval does not result in a true R-R interval being flagged as a false R-R interval for being twice the duration of a neighboring R-R interval. The specific duration threshold that is used at step 408 can be patient specific, and/or can be arrhythmia specific. More specifically, different duration thresholds can be used for different types of arrhythmias. For example, a first duration threshold can be used where a detected arrhythmia is a bradycardia, a second duration threshold can be used where the detected arrhythmia is a tachycardia, a third duration threshold can be used where the detected arrhythmia is AF, a fourth duration threshold can be used where the detected arrhythmia is VF etc.

At step 410, for the R-R interval being analyzed a ratio ("r") is calculated relative to each of the N neighboring R-R intervals (e.g., the immediately preceding M intervals and immediately following M intervals), or more generally, relative to each R-R interval in a set of N neighboring R-R intervals, where N is at least 6, and M is at least 3. The result of step 410 is a set of ratios.

Step 412 involves removing, from the set of ratios, any ratio that when rounded to its closest integer rounds to less than two. In other words, any ratio (in the set of ratios) having a value that is less than 1.5 is removed from the set, since when rounded to the closest integer it would round to one, which is less than two.

Step 414 involves determining an indicator of a difference between a duration of the R-R interval (selected at step 404 for analysis) and those of its N neighboring R-R intervals that were not removed at step 412. In certain embodiments, the indicator of the difference between the analyzed R-R interval and its neighboring R-R intervals (that were not removed at step 412) is a percent difference that is calculated using the equation:

$$\% \text{ difference} = 100 \times |r - \text{round}(r)| / \text{round}(r)$$

where,
r is the ratio of the analyzed R-R interval relative to a neighboring R-R interval, and
round (r) is the calculated ratio rounded to the nearest integer.

Step 416 involves determining whether the % differences (or more generally, indicators of the difference), for at least a specified number X of the ratios in the set, is less than a specified difference threshold (e.g., <10%). This criterion ensures that the interval in question is reasonably close to an integer multiple of at least X of its neighboring R-R intervals, where the integer multiple is at least 2, and where X is a specified integer that is at least 1. If the answer to the determination at step 416 is Yes, then flow goes to step 418 and the R-R interval being analyzed is classified as being a false R-R interval associated with R-wave undersensing or AV conduction block. If the answer to the determination at step 416 is No, then flow goes to step 420. Still referring to step 416, the minimum percent difference threshold may be programmable depending on the clinical need, as noted above. Similarly, the value for X may be programmable depending on the clinical need. For example, the specified difference threshold can be 10%, and the value for X can be 1, if arrhythmia (e.g., AF) sensitivity is important; or the specified difference threshold can be 15%, and the value for X can be 2, if specificity is more important that sensitivity. The specific difference threshold and/or value for X that is/are used at step 416 can be patient specific, and/or can be arrhythmia specific. More specifically, different difference thresholds and/or values for X can be used for different types of arrhythmias. For example, a first difference threshold and a first value for X can be used where a detected arrhythmia is a bradycardia, a second difference threshold and a second value for X can be used where the detected arrhythmia is a tachycardia, a third difference threshold and a third value for X can be used where the detected arrhythmia is AF, etc.

At step 420 there is a determination of whether there is any additional R-R interval in the ordered list of R-R intervals (obtained at step 402) to analyze. If the answer to step 420 is Yes, then flow returns to step 404 and the next R-R interval in the list (obtained at step 402) is selected for analysis. In this manner, steps 404 through 420 are repeated until the answer to the determination at step 420 is No, at which point flow goes to step 422 in FIG. 4B.

Figure 4B:
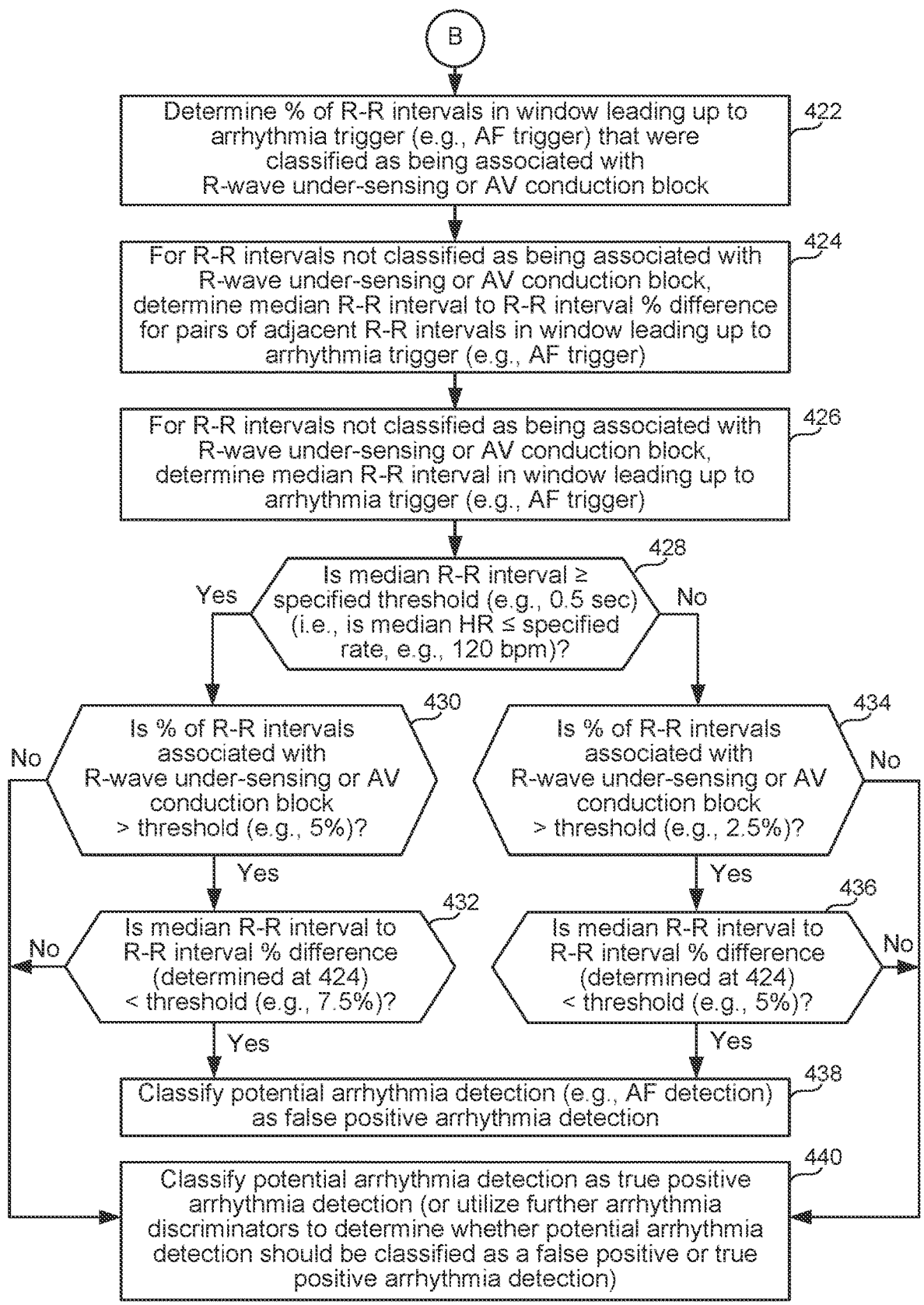

Referring to FIG. 4B, at step 422 there is a determination of what percent of the R-R intervals, in the window leading up to the detection of the potential arrhythmic episode, were classified as being associated with at least one of R-wave undersensing or AV conduction block. For an example, if there were 40 R-R intervals in the window leading up to the detection of the potential arrhythmic episode, and 10 of those R-R intervals were classified as being associated with at least one of R-wave undersensing or AV conduction block, then the result of step 422 would be 25 percent. The percent that is determined at step 422 can also be referred to herein as the R-wave undersensing/block percent.

At step 424 there is a determination of the median R-R interval to R-R interval percentage difference, for those R-R intervals (in the window leading up to the detection of the potential arrhythmic episode, e.g., potential AF episode) that were not classified as being associated with at least one of R-wave undersensing or AV conduction block. Continuing with the above example, where 10 of 40 R-R intervals were classified as being associated with at least one of R-wave undersensing or AV conduction block, at step 424 there is a determination of the median R-R interval to R-R interval percentage difference for the remaining 30 R-R intervals (that were not classified as being associated with R-wave undersensing/block). This would involve determining the % differences between the $1^{st}$ and $2^{nd}$ R-R intervals, between the $2^{nd}$ and $3^{rd}$ R-R intervals, between the $3^{rd}$ and $4^{th}$ R-R intervals, . . . between the 29th and 30th R-R intervals, thereby resulting in 29 separate % differences, or more generally Z−1 separate % differences (where Z is how many R-R intervals within the window were not classified as being associated with R-wave undersensing/block). To find the median of the Z−1 separate % differences (e.g., the 29 separate % differences), the % differences can be arranged in order from least to greatest, and the median is the value that is halfway into the set, i.e., the middlemost value. If there is an even number of values in the data set, then the median can be determined by determining the mean (average) of the two middlemost numbers, or selecting either one of the two middlemost numbers, depending upon the specific implementation. The idea here is that R-R intervals associated with "true" R-waves should be relatively consistent and not vary wildly when a patient is not experiencing an actual arrhythmic episode (e.g., an actual AF episode). If the remaining R-R intervals (i.e., those not associated with R-wave undersensing/block) are not relatively consistent and vary wildly, then that is indicative of the patient likely having experienced an actual arrhythmic episode (e.g., an actual AF episode).

At step 426 there is a determination of the median R-R interval of those R-R intervals (in the window leading up to the detection of the potential arrhythmic episode, e.g., the potential AF episode) that were not classified as being associated with at least one of R-wave undersensing or AV conduction block (aka R-wave undersensing/block).

At step 428 there is a determination of whether the median R-R interval (determine at step 426) is greater than or equal to a specified duration threshold, such as 0.5 seconds. This is equivalent to determining whether the median heart rate (HR) for the patient (corresponding to the R-R intervals in the window leading up to the detection of the potential arrhythmic episode, which were not classified as being associated with R-wave undersensing/block) is less than or equal to a specified HR threshold, e.g., 120 beats per minute (bpm). If the answer to the determination at step 428 is Yes, then flow goes to step 430. If the answer to the determination at step 430 is No, then flow goes to step 434.

At step 430 there is a determination whether the R-wave undersensing/block percent (that was determined at step 422) is greater than a first specified percent threshold, e.g., >5%. This criterion is used to determine whether enough R-waves were classified as being associated with R-wave undersensing/block, such that they may have influenced the initial arrhythmia detection/trigger (e.g., the initial AF detection/trigger). If the answer to the determination at step 430 is Yes, then flow goes to step 432.

At step 432 there is a determination of whether the median R-R interval to R-R interval % difference (that was determined at step 424) is less than a first median percent difference threshold, e.g., <7.5%. This criterion is used to determine whether the R-R intervals associated with "true" R-waves (i.e., not associated with R-wave undersensing/block) are relatively consistent and do not vary wildly, which would be indicative of the patient not experiencing an actual AF or VF episode. Explain another way, during actual AF or VF, some R-R intervals may still be classified as being associated with R-wave undersensing/block if the R-R intervals randomly are similar to integer-multiples of neighboring R-R intervals. This criterion checks whether, without these R-wave undersensing/block-related R-R intervals, the rhythm is otherwise stable. If the answer to the determination at step 432 is Yes, then flow goes to step 438. At step 438 the potential AF or VF episode is classified as a false positive detection. Explained another way, at step 438 the AF or VF trigger or detection of the potential AF or VF episode is rejected. The order of steps 430 and 432 can be reversed. Similarly, the orders of steps 422, 424, and 426 can be rearranged.

If the answer to either one of steps 430 or 432 is No, then flow goes to step 440. At step 440 the potential arrhythmic episode can be classified as a true arrhythmic episode, or a confidence level or probability that the potential arrhythmic episode was actually a true arrhythmic episode can be increased, or one or more further arrhythmia discriminators can be used to determine whether the potential arrhythmia detection should be classified as a true positive or false positive arrhythmia detection.

Referring back to step 428, if the answer to the determination at step 428 is No, then flow goes to step 434. At step 434 there is a determination whether the R-wave undersensing/block percent (that was determined at step 422) is greater than a second specified percent threshold, e.g., >2.5%, which is less than the first specified percent threshold used at step 430. If the answer to the determination at step 434 is Yes, then flow goes to step 436.

At step 436 there is a determination of whether the median R-R interval to R-R interval % difference (that was determined at step 424) is less than a second median percent difference threshold, e.g., <5%, which is less than the first median percent difference threshold used at step 432. If the answer to the determination at step 436 is Yes, then flow goes to step 438, at which the potential arrhythmia (e.g., AF or VF) episode is classified as a false positive detection. The order of steps 434 and 436 can be reversed.

If the answer to either one of steps 434 or 436 is No, then flow goes to step 440. As noted above, at step 440 the potential arrhythmic episode can be classified as a true arrhythmic episode, or a confidence level or probability that the potential arrhythmic episode was actually a true arrhythmic episode can be increased, or one or more further arrhythmia discriminators can be used to determine whether the potential arrhythmia detection should be classified as a true positive or false positive arrhythmia detection.

The thresholds used in the branch at the right in FIG. 4B (which includes steps 434 and 436) are lower than the respective thresholds used in the branch at the left in FIG. 4B (which includes step 430 and 432). This is to account for there being less of a chance that a potential arrhythmia detection is a false positive, if the answer to the determination at step 428 is No. More specifically, the second specified percent threshold (e.g., 2.5%) used at step 434 is less than the first specified percent threshold (e.g., 5%) used at step 430 to account for the fact that an AF or VF detection algorithm (used to detect a potential AF or VF episode in the first place) likely has a greater sensitivity at higher heart rates and can be easily triggered by a few just a few under-sensed/blocked R-waves. Additionally, the second median percent difference threshold (e.g., 5%) used at step 436 is less than the first median percent difference threshold (e.g., 7.5%) used at step 432 to be more conservative when labeling faster rhythms as being associated with R-wave undersensing/block, as fast rhythms are more likely to truly be AF or VF.

Step 428 and the branch on the right (which includes steps 434 and 436) enable different thresholds to be used for higher heart rates (HRs) (i.e., shorter R-R intervals) than for lower HRs (i.e., longer R-R intervals), as can be appreciated from the flow diagram. In an alternative embodiment, step 428 and the branch on the right (which includes steps 434 and 436) are eliminated, in which case flow would go directly from step 426 to step 430. In such an alternative embodiments, the same thresholds would be used for both low and high HRs (i.e., for both long and short R-R intervals).

There are various values and thresholds that are used in the various steps summarized above with reference to FIG. 4, which values and/or thresholds can be adjusted to increase or reduce the sensitivity of R-wave undersensing identification and/or to increase or reduce the sensitivity of arrhythmic episode detection rejection (i.e., when determining whether a detection of an arrhythmic episode was a false positive detection). An increase in sensitivity typically results in a reduction in specificity, and a decrease in the sensitivity typically results in an increase in the specificity. A desired balance between sensitivity and specificity can be patient specific and/or arrhythmia specific. In accordance with certain embodiments, there is a respective different set of values and thresholds specified for use with each of a plurality of different types of arrhythmias. Where an arrhythmia is potentially life threatening, such as VF, the set of values and thresholds can be defined to have a low sensitivity, so as to avoid rejecting or ignoring a potentially life threatening episode and withholding appropriate therapy, such as a defibrillation shock. The value of X that is used at step 416 can be increased to reduce the sensitivity of R-wave undersensing, or the value of X that is used at step 416 can be decreased to increase the sensitivity of R-wave undersensing. For another example, the difference threshold that is used at step 416 can be increased to increase the sensitivity of R-wave undersensing identification (to allow for a greater margin of error for the percent differences), or the difference threshold that is used at step 416 can be reduced to decrease the sensitivity of R-wave undersensing identification. The percent threshold(s) used at step 430 and/or 434 can be increased to reduce the sensitivity of arrhythmic episode rejection, or percent threshold(s) used at step 430 and/or 434 can be decreased to increase the sensitivity of arrhythmic episode rejection. It is noted that the terms decrease and reduce are used interchangeably herein.

In accordance with certain embodiments, an IMD may perform the method described above with reference to FIG. 4 in response to an AF episode (or some other type of arrhythmic episode) being detected. Where the steps summarized above with reference to FIG. 4 (which included FIGS. 4A and 4B) are performed in response to an arrhythmia trigger (e.g., an AF trigger), some of the steps may be skipped, depending on the specific type of potential arrhythmic episode that was detected. For example, steps 424, 426 and 428 (and the right branch that includes steps 434 and 436) are primarily helpful where the type of potential arrhythmic episode that was detected is AF or VF, in which cases there should be a relatively high variability in R-R intervals if the arrhythmia detections were true positive detections. When used with other types of arrhythmias, such as bradycardia or tachycardia, flow can jump from step 422 to step 430 (i.e., steps 424, 426 and 428 can be skipped, and steps 434 and 436 are not needed). Accordingly, between steps 422 and 424 there can be a determination step (not shown) that determines whether the arrhythmia trigger was an AF or VF trigger. If the answer to that determination is Yes, then flow would go to step 424, and if the answer to that determination is No, then flow would jump to step 430.

In accordance with certain embodiments, an IMD may perform the method described above with reference to FIG. 4 in response to an AF episode (or some other type of arrhythmic episode) being detected. The detection of an arrhythmic episode can also be referred to as an arrhythmia trigger, e.g., the detection of an AF episode can also be referred to as an AF trigger. Such an IMD may be configured to transmit, to an external device that is communicatively coupled to a patient care network, data corresponding to an AF episode (or other type of arrhythmic episode) that is detected by the IMD. In certain such embodiments, the IMD does not (is prevented from) transmitting (to the external device that is communicatively coupled to the patient care network) data corresponding to an AF episode (or other type of arrhythmic episode) that is detected by the IMD, but is thereafter determined by the IMD as being a false positive detection. The IMD can also be configured to allow overwriting in the memory of data corresponding to a potential arrhythmic episode (e.g., a potential AF episode) that was detected by the IMD but is thereafter determined by the IMD as being a false positive detection. Alternatively, the IMD can prevent storing in the memory of data corresponding to a potential arrhythmic episode (e.g., a potential AF episode)

that is detected by the IMD but is thereafter determined by the IMD as being a false positive detection.

In accordance with certain embodiments, the medical device (e.g., IMD) that performs the method described above with reference to FIG. 4 may monitor the HR of a patient based on R-R intervals identified from a segment of an EGM or ECG, and the medical device can determine based on the results of the method whether a monitored HR is inaccurate due to oversensing and thus should be ignored or recalculated. For an example, if at least a specified amount of R-R intervals classified as being associated with R-wave undersensing/AV conduction block exceeds a corresponding threshold, the medical device can conclude that a HR that was determined based on sensed interval is inaccurate and should not be used, or should be recalculated.

An implementation of an embodiment of the present technology described above was tested to determine whether and to what extend the present technology can be used to reduce the reporting of false positive AF detections. EGM segments corresponding to numerous detected AF episodes (that were detected by Confirm Rx™ ICMs) were manually adjudicated as either "true" or "false" positive AF detections. Of the numerous episodes, about 25 percent were adjudicated as true AF episodes (i.e., as true positives), and the remaining about 75 percent were adjudicated as non-AF episodes (i.e., as false positives). Of the true AF episode, less than 1 percent were incorrectly classified (aka flagged) as a false positive detection using an embodiment of the present technology summarized above with reference to FIG. 4. Of the false AF episodes, almost 50 percent were correctly classified (aka flagged) as false positive detections using an embodiment of the present technology summarized above with reference to FIG. 4.

The example thresholds described herein were conservatively chosen to limit the number of true AF episodes being incorrectly classified as false detections due to R-wave undersensing/block. However, the basic logic of the embodiments described herein can extend beyond the above limitations. The specific values of each threshold can be more systematically optimized for a narrow patient population, a broader patient population, or for individual patients. Accordingly, embodiments of the present technology described herein should not be limited to use with the example thresholds described herein. As explained above, in accordance with certain embodiments, there can be a respective different set of values and thresholds specified for use with each of a plurality of different types of arrhythmias.

Figure 5:
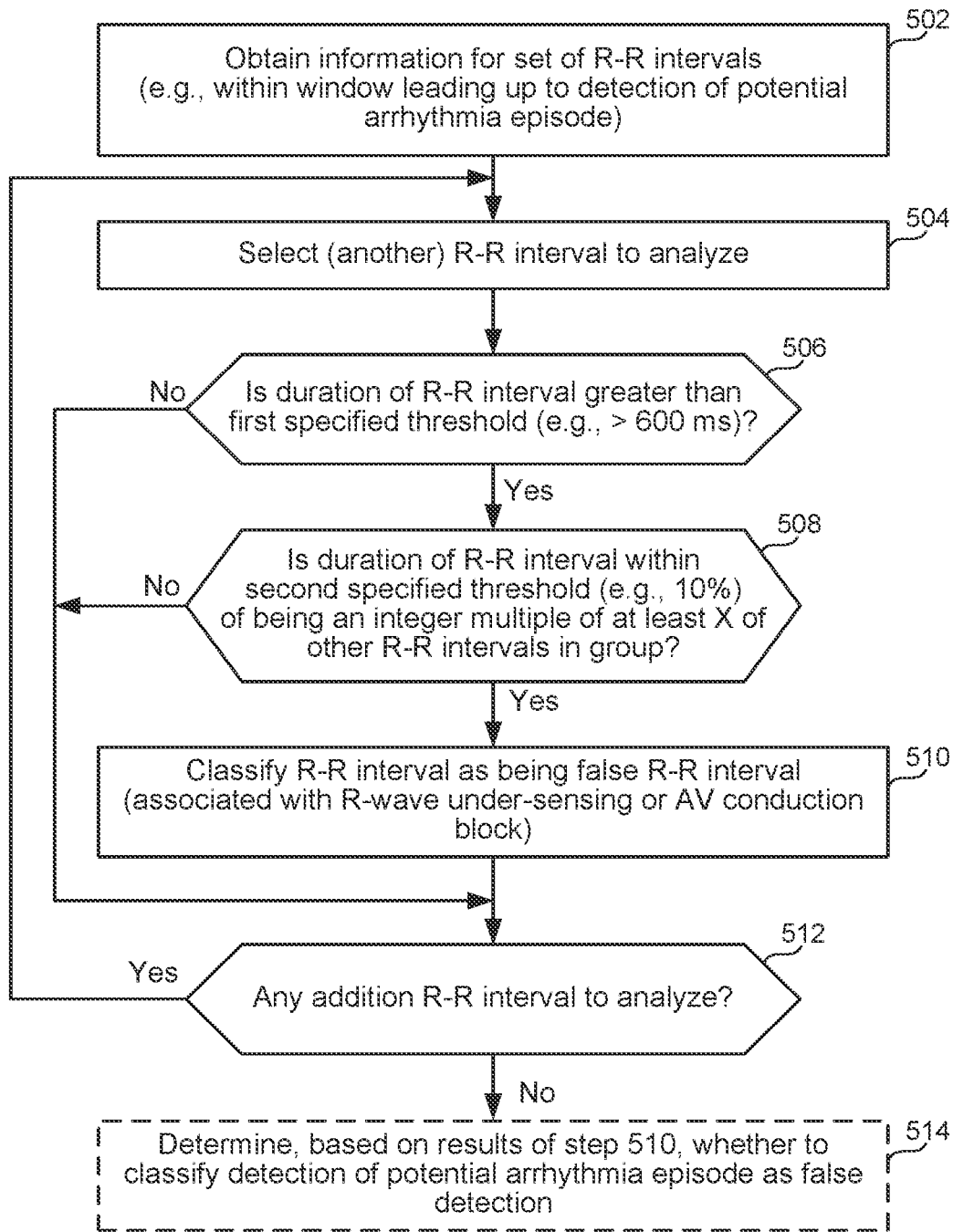
FIG. 5 is a high level flow diagram that is used to summarize methods, according to various embodiments of the present technology, for use by a device or system that monitors cardiac activity, wherein such a method can be used to identify false R-R intervals and/or false AF detections.

The high level flow diagram of FIG. 5 is used to summarize certain methods for use by a device or system that monitors cardiac activity, wherein such a method can be used to identify false R-R intervals and/or false arrhythmia detections (e.g., false AF detections). The embodiments summarized above with reference to FIG. 4 are specific implementations of the methods summarized with reference to FIG. 5.

Referring to FIG. 5, step 502 involves obtaining information for a set of R-R intervals, wherein each of the R-R intervals has a respective duration, and each of the R-R intervals may be a true R-R interval or a false R-R interval. Such a set of R-R intervals can be, e.g., the R-R intervals within a window (e.g., a 30 second window) leading up to the detection of a potential arrhythmic episode (e.g., a potential AF episode), but is not limited thereto. This set should include at least three R-R intervals, but will likely include much more, e.g., at least twenty R-R intervals, but not limited thereto.

Step 504 involves selecting an R-R interval to analyze. Step 506 involves determining whether the duration of the R-R intervals is greater than a first specified threshold (e.g., 600 ms), and step 508 involves determining whether the duration of the R-R interval is within a second specified threshold (e.g., 10%) of being an integer multiple of at least X of the other R-R intervals for which information is obtained, wherein the integer multiple is at least 2, and wherein X is a specified integer that is 1 or greater. Step 510 involves classifying one of the R-R intervals as being a false R-R interval, in response to both the duration of the R-R interval being greater than the first specified threshold (e.g., 600 ms), and the duration of the R-R interval being within the second specified threshold (e.g., 10%) of being an integer multiple of at least X of the other R-R intervals for which information is obtained. At step 512 there is a determination of whether there is an additional R-R interval to analyze. If the answer to the determination at step 512 is Yes, then flow returns to step 504. At optional step 514 there is a determination of whether to classify a potential AF episode (or other type of arrhythmic episode) as a false detection, e.g., if at least a specified percent or number of R-R intervals are classified as false R-R intervals, and/or if after removing the false R-R intervals, the variability and/or other characteristics of the remaining R-R intervals are indicative of the potential arrhythmic episode (e.g., the potential AF episode) actually being a true arrhythmic episode (e.g., a true AF episode).

Figure 6:
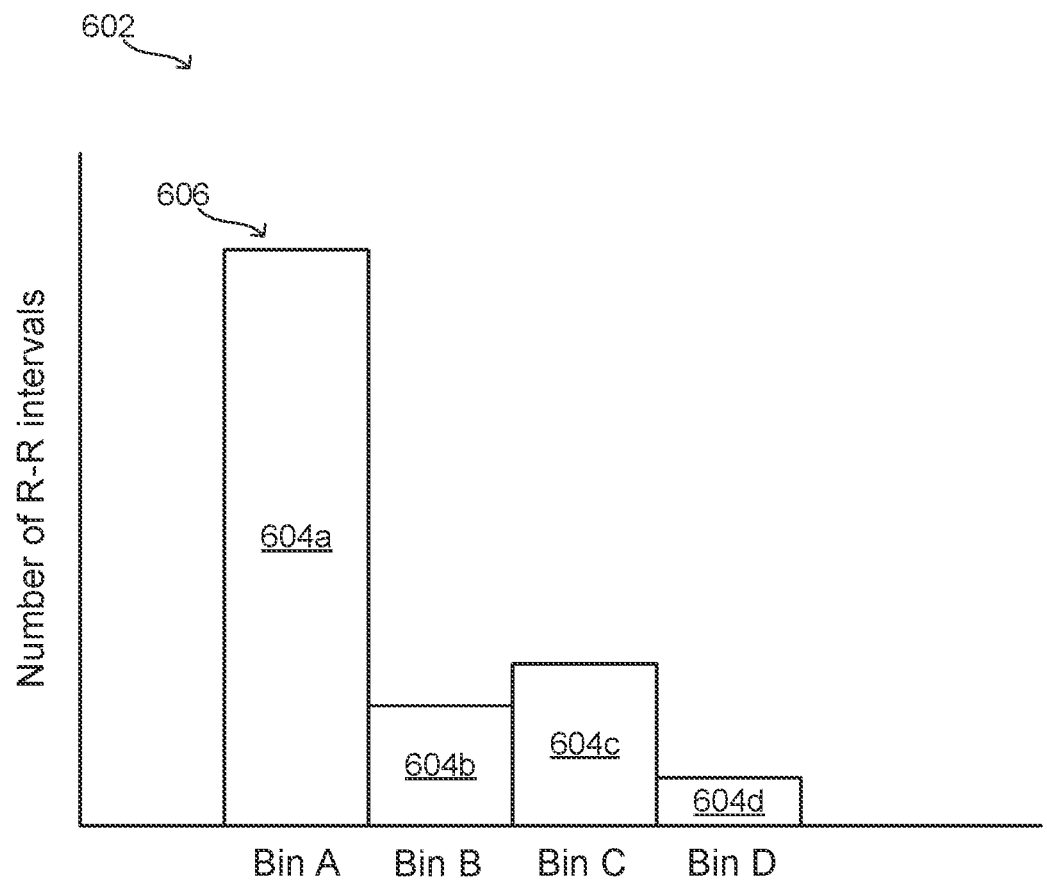
FIG. 6 illustrates an exemplary histogram that can be generated and used to determine which group of R-R intervals within a set of R-R intervals is the dominant group, and thus, likely includes true R-R intervals that can be compared to R-R intervals outside the dominant group to determine whether the R-waves outside the dominant group are false R-R intervals associated with R-wave undersensing or AV conduction block.

In accordance with certain embodiments, between steps 502 and 504, the R-R intervals in the set are grouped into two or more groups based on the durations of the R-R intervals, such that R-R intervals that are within a third specified threshold (e.g., within 15%) of one another are grouped into a same one of the groups, and the group that includes a greatest number of R-R intervals is classified as a dominant group. In such embodiments, the other R-R intervals in the group, that are used at instances of step 508, are the R-R intervals that are within the dominant group, which are most likely true R-R intervals. Such a grouping can result in a histogram, such as the one shown in FIG. 6. Referring to FIG. 6, the example histogram 602 shown therein includes a plurality of bins 604a, 604b, 604c, 604d, each of which corresponds to R-R intervals that are within the third specified threshold (e.g., 15% or 20%) of one another. Using such a histogram, the dominant group 606 can be identified by identifying the one of the bins having the greatest number of R-R intervals therein. It can be presumed that R-R intervals that are within the dominant group are true R-R intervals. Accordingly, in certain embodiments, at instances of step 504 (in FIG. 5), it may be that only R-R intervals that are not in the dominant group are selected for analysis. Unless otherwise specified, when selecting an R-R interval at instances of step 504, the R-R intervals need not be selected in any specific order.

There are various values and thresholds that are used in the various steps summarized above with reference to FIG. 5, which values and/or thresholds can be adjusted to increase or reduce the sensitivity of R-wave undersensing identification and/or to increase or reduce the sensitivity of arrhythmic episode detection rejection (i.e., when determining whether a detection of an arrhythmic episode was a false positive detection).

Embodiments of the present technology described herein can be used with various types of IMDs, including, but not limited to, an insertable cardiac monitor (ICM), a cardiac pacemaker to which one or more leads is/are attached, a leadless cardiac pacemaker (LCP), or an implantable cardioverter defibrillator (ICD). Such an ICD can be a transvascular ICD, or a nonvascular ICD, wherein the nonvascular ICD can be a subcutaneous (SubQ) ICD. Where embodiments of the present technology are implemented by an ICM, such embodiments can be used, e.g., to reduce the number of false positive AF detections that are transmitted from the ICM to a patient care network for clinician review. This is beneficially because false positive AF detections are highly undesirable, as the burden of sorting through large numbers of clinically irrelevant episodes of AF can be time consuming and costly. Where embodiments of the present technology are used by an ICD, or by an IMD in communication with an ICD, such embodiments can reduce how often defibrillation shocks are delivered in response to false positive AF detections. This is beneficial because defibrillation shocks are typically painful, and delivering such shocks in response to false positive AF detections subjects the patient to unnecessary shocks and may prematurely deplete the energy stored in a battery.

In accordance with certain embodiments of the present technology, in response to a potential bradycardia episode or a potential cardia pause episode being detected, one of the techniques summarized above with reference to FIGS. 4 and 5 is performed to determine whether the potential arrhythmic episode detection was potentially caused by AV conduction block. In other words, embodiments of the present technology described herein can be used identify a potential AV conduction block. When used for detecting potential AV conduction block, steps 424, 426 and 428 (and the right branch that includes steps 434 and 436) should be skipped. Such an embodiment alone will not distinguish R-wave undersensing from AV conduction block, but such an embodiment can be used as a first-stage screening to identify potential AV conduction block, and then another known or future developed technique, such as an EGM based technique can be used to determine whether or not AV conduction block actually occurred. Such an EGM based technique, which is used to determine whether or not AV conduction block actually occurred, can look for abnormalities in a PR interval, and/or analyze the relationship between P-waves and QRS complexes, but is not limited thereto.

Figure 7:
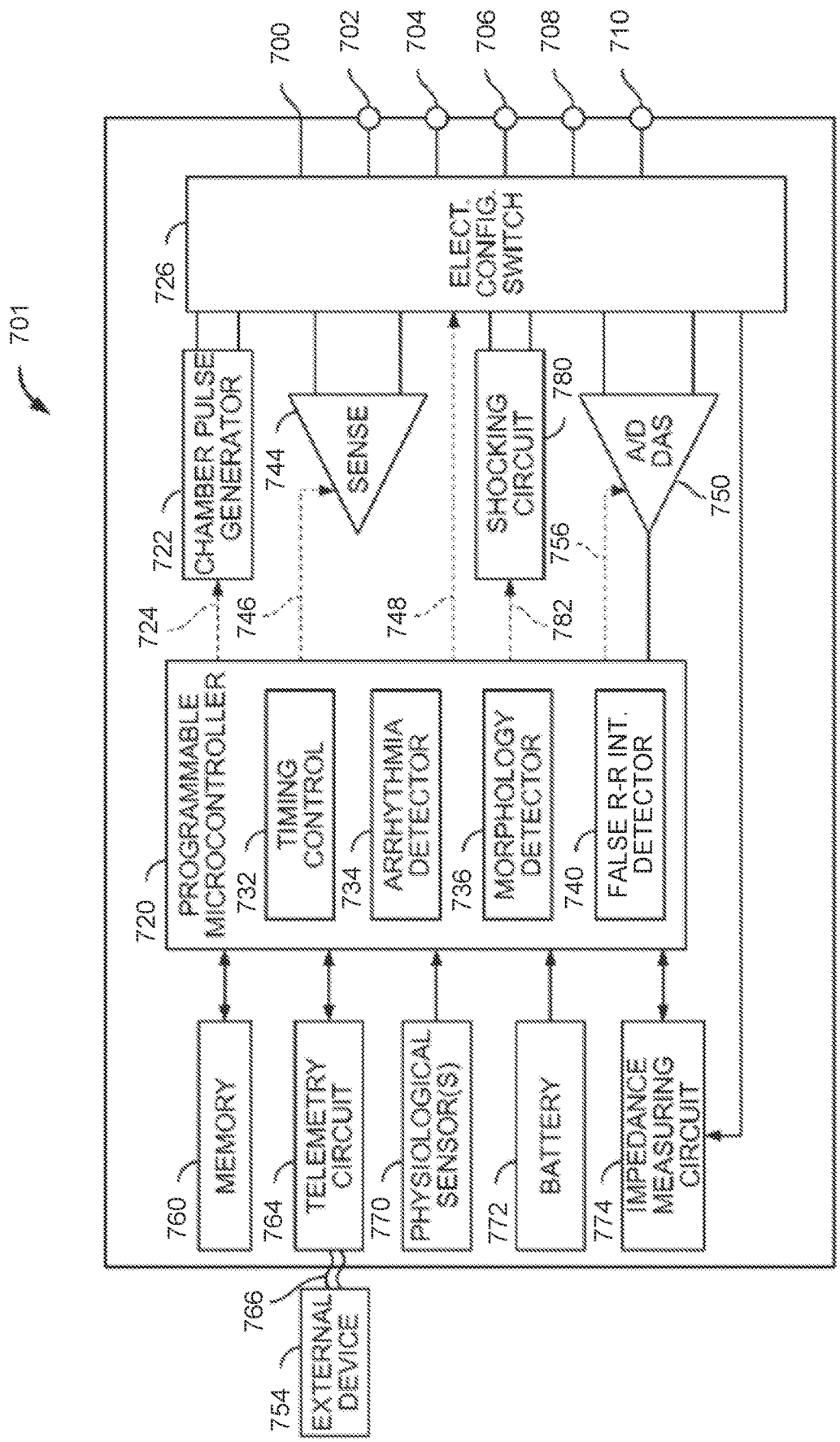
FIG. 7 shows a block diagram of one embodiment of an IMD that is implanted into a patient in accordance with certain embodiments of the present technology.

An embodiment of the present technology, summarized above with reference to FIGS. 4 and 5, can be used to confirm or reject a detection of a potential arrhythmic episode. In other words, such embodiments can be used to distinguish false positive arrhythmia detections from true positive arrhythmia detections. Additionally, or alternatively, embodiments of the present technology described herein can be used to help detect an arrhythmic episode more accurately in the first place. More specifically, one of the techniques described herein can be performed continuously in conjunction with one or more arrhythmia detection techniques. In other words, one of the techniques described herein can interact with one or more arrhythmia detection techniques in real-time, or near real-time, rather than waiting until an arrhythmia trigger (e.g., an AF trigger) to perform one of the techniques described herein with reference to FIGS. 4 and 5. For example, assume an arrhythmia detection algorithm is on its way to triggering an AF detection and one of the techniques described herein identifies substantial R-wave undersensing or AV conduction block. In response thereto, AF trigger criteria in the arrhythmia detection technique can be appropriately adjusted, or the arrhythmia detection technique can stop being performed in response to there being a determination that the R-R intervals being analyzed are inaccurate due to R-wave oversensing or AV conduction block. Other variations are also possible and within the scope of the embodiments described herein. FIG. 7 shows a block diagram of one embodiment of an IMD that is implanted into a patient in accordance with a certain embodiment of the present technology. The IMD 701 may be implemented as a full-function biventricular pacemaker and defibrillator, equipped with both atrial and ventricular sensing and pacing circuitry for four chamber sensing and stimulation therapy (including both pacing and shock treatment). Optionally, the IMD 701 may provide full-function cardiac resynchronization therapy. Alternatively, the IMD 701 may be implemented with a reduced set of functions and components. For instance, the IMD may be implemented without pacing, e.g., if the IMD is an ICM. The IMD 701 can be coupled to one or more leads for single chamber or multi-chamber pacing and/or sensing. Alternatively, the IMD 701 can be an LCP that includes electrodes located on or very close to a housing 700 of the IMD 701.

The IMD 701 has a housing 700 to hold the electronic/computing components. The housing 700 (which is often referred to as the "can", "case", "encasing", or "case electrode") may be programmably selected to act as the return electrode for certain stimulus modes. The housing 700 may further include a connector (not shown) with a plurality of terminals 702, 704, 706, 708, and 710. The terminals may be connected to electrodes that are located in various locations on the housing 700 or to electrodes located on leads. The IMD 701 includes a programmable microcontroller 720 that controls various operations of the IMD 701, including cardiac monitoring and/or stimulation therapy. The microcontroller 720 includes a microprocessor (or equivalent control circuitry), RAM and/or ROM memory, logic and timing circuitry, state machine circuitry, and I/O circuitry.

The IMD 701 further includes a pulse generator 722 that generates stimulation pulses and communication pulses for delivery by one or more electrodes coupled thereto. The pulse generator 722 is controlled by the microcontroller 720 via a control signal 724. The pulse generator 722 may be coupled to the select electrode(s) via an electrode configuration switch 726, which includes multiple switches for connecting the desired electrodes to the appropriate I/O circuits, thereby facilitating electrode programmability. The switch 726 is controlled by a control signal 728 from microcontroller 720.

In the embodiment of FIG. 7, a single pulse generator 722 is illustrated. Optionally, the IMD may include multiple pulse generators, similar to the pulse generator 722, where each pulse generator is coupled to one or more electrodes and controlled by the microcontroller 720 to deliver select stimulus pulse(s) to the corresponding one or more electrodes.

The microcontroller 720 is illustrated as including timing control circuitry 732 to control the timing of the stimulation pulses (e.g., pacing rate, atrio-ventricular (AV) delay, atrial interconduction (A-A) delay, or ventricular interconduction (V-V) delay, etc.). The timing control circuitry 732 may also be used for the timing of refractory periods, blanking intervals, noise detection windows, evoked response windows, alert intervals, marker channel timing, and so on. The microcontroller 720 also has an arrhythmia detector 734 for detecting arrhythmia conditions and a morphology detector 736. Although not shown, the microcontroller 720 may further include other dedicated circuitry and/or firmware/software components that assist in monitoring various conditions of the patient's heart and managing pacing therapies. The microcontroller 720 is also shown as including a false R-R interval detector 740, which can be used to perform the embodiments of the present technology described above with reference to FIGS. 1-6. The false R-R interval detector 740 can more generally be implemented using hardware, software, firmware, and/or combinations thereof. The microcontroller can include a processor. The microcontroller, and/or the processor thereof, can be used to perform the methods of the present technology described herein.

The IMD 701 can be further equipped with a communication modem (modulator/demodulator) to enable wireless communication with the remote slave pacing unit. The modem may include one or more transmitters and two or more receivers. In one implementation, the modem may use low or high frequency modulation. As one example, modem may transmit implant-to-implant (i2i) messages and other signals through conductive communication between a pair of electrodes. Such a modem may be implemented in hardware as part of the microcontroller 720, or as software/firmware instructions programmed into and executed by the microcontroller 720. Alternatively, the modem may reside separately from the microcontroller as a standalone component.

The IMD 701 includes a sensing circuit 744 selectively coupled to one or more electrodes, that perform sensing operations, through the switch 726 to detect the presence of cardiac activity in the right chambers of the heart. The sensing circuit 744 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the unit to sense low amplitude signal characteristics of atrial fibrillation. The switch 726 determines the sensing polarity of the cardiac signal by selectively closing the appropriate switches. In this way, the clinician may program the sensing polarity independent of the stimulation polarity.

The output of the sensing circuit 744 is connected to the microcontroller 720 which, in turn, triggers or inhibits the pulse generator 722 in response to the presence or absence of cardiac activity. The sensing circuit 744 receives a control signal 746 from the microcontroller 720 for purposes of controlling the gain, threshold, polarization charge removal circuitry (not shown), and the timing of any blocking circuitry (not shown) coupled to the inputs of the sensing circuitry.

In the embodiment of FIG. 7, a single sensing circuit 744 is illustrated. Optionally, the IMD may include multiple sensing circuits, similar to the sensing circuit 744, where each sensing circuit is coupled to one or more electrodes and controlled by the microcontroller 720 to sense electrical activity detected at the corresponding one or more electrodes. The sensing circuit 744 may operate in a unipolar sensing configuration or in a bipolar sensing configuration.

The IMD 701 further includes an analog-to-digital (ND) data acquisition system (DAS) 750 coupled to one or more electrodes via the switch 726 to sample cardiac signals across any pair of desired electrodes. Data acquisition system 750 is configured to acquire intracardiac electrogram signals, convert the raw analog data into digital data, and store the digital data for later processing and/or telemetric transmission to an external device 754 (e.g., a programmer, local transceiver, or a diagnostic system analyzer). Data acquisition system 750 is controlled by a control signal 756 from the microcontroller 720.

The microcontroller 720 is coupled to a memory 760 by a suitable data/address bus. The programmable operating parameters used by the microcontroller 720 are stored in memory 760 and used to customize the operation of the IMD 701 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy.

The operating parameters of the IMD 701 may be non-invasively programmed into memory 760 through a telemetry circuit 764 in telemetric communication via a communication link 766 with an external device 754. The telemetry circuit 764 allows intracardiac electrograms and status information relating to the operation of the IMD 701 (as contained in the microcontroller 720 or memory 760) to be sent to the external device 754 through the communication link 766.

The IMD 701 can further include magnet detection circuitry (not shown), coupled to the microcontroller 720, to detect when a magnet is placed over the unit. A magnet may be used by a clinician to perform various test functions of IMD 701 and/or to signal the microcontroller 720 that the external device 754 is in place to receive or transmit data to the microcontroller 720 through the telemetry circuit 764.

The IMD 701 can further include one or more physiological sensors 770. Such sensors are commonly referred to as "rate-responsive" sensors because they are typically used to adjust pacing stimulation rates according to the exercise state of the patient. However, the physiological sensor(s) 770 may further be used to detect changes in cardiac output, changes in the physiological condition of the heart, or diurnal changes in activity (e.g., detecting sleep and wake states). Signals generated by the physiological sensor(s) 770 are passed to the microcontroller 720 for analysis. The microcontroller 720 responds by adjusting the various pacing parameters (such as rate, AV Delay, V-V Delay, etc.) at which the atrial and ventricular pacing pulses are administered. While shown as being included within the IMD 701, one or more physiological sensor(s) 770 may be external to the IMD 701, yet still be implanted within or carried by the patient. Examples of physiologic sensors include sensors that, for example, sense respiration rate, pH of blood, ventricular gradient, activity, position/posture, minute ventilation (MV), and so forth.

A battery 772 provides operating power to all of the components in the IMD 701. The battery 772 is preferably capable of operating at low current drains for long periods of time, and is capable of providing high-current pulses (for capacitor charging) when the patient requires a shock pulse (e.g., in excess of 2 A, at voltages above 2 V, for periods of 10 seconds or more). The battery 772 also desirably has a predictable discharge characteristic so that elective replacement time can be detected. As one example, the IMD 701 employs lithium/silver vanadium oxide batteries.

The IMD 701 further includes an impedance measuring circuit 774, which can be used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. The impedance measuring circuit 774 is coupled to the switch 726 so that any desired electrode may be used. In this embodiment the IMD 701 further includes a shocking circuit 780 coupled to the microcontroller 720 by a data/address bus 782.

The embodiments of the present technology described above were primarily described as being used with an implantable medical device or system that monitors HR and/or for one or more types of arrhythmic episodes based on R-R intervals, which as noted above can be, e.g., true R-R intervals or false (e.g., over-sensed) R-R intervals. Such embodiments of the present technology can alternatively be used with a non-implantable device or system (aka an external device or system) that includes at least two electrodes in contact with a person's skin and is used to monitor HR and/or for one or more types of arrhythmic episodes based on R-R intervals. More specifically, such embodiments can alternatively be used with or be implemented by a user wearable device, such as a wrist worn device, or a user wearable device designed to be worn on one or more other portions of a person's body besides a wrist, e.g., on an ankle, an upper arm, or a chest, but not limited thereto. Such a user wearable device can include electrodes that are configured to contact a person's skin, sensing circuitry coupled to the electrodes and configured to obtain a signal indicative of electrical activity of a patient's heart, and at least one of a processor or controller that is configured to perform one or more of the algorithms described above. Such a user wearable device (or more generally an external device or system) can monitor for AF and/or other types of arrhythmia(s) and determine when there is a false positive detection. Additionally, or alternatively, such a user wearable device (or more generally an external device or system) can monitor a person's HR and determine when measures of HR are likely inaccurate due to oversensing. A user wearable device can both obtain a signal indicative of electrical activity of a patient's heart and monitor a person's HR and/or for arrhythmia(s) based on R-R intervals obtained from the obtained signal. Alternatively, a user wearable device can be communicatively coupled to another external device, such as a smartphone or tablet computer, and the other external device can obtain the signal from the user wearable device and monitor a person's HR and/or for arrhythmia(s) based on R-R intervals. The user wearable device or other external device or system can determine when there may be a false positive and/or when a measured HR may be inaccurate due to oversensing. Other implementations of such an external device or system are also possible and within the scope of the embodiments described herein.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, it is noted that the term "based on" as used herein, unless stated otherwise, should be interpreted as meaning based at least in part on, meaning there can be one or more additional factors upon which a decision or the like is made. For example, if a decision is based on the results of a comparison, that decision can also be based on one or more other factors in addition to being based on results of the comparison.

Embodiments of the present technology have been described above with the aid of functional building blocks illustrating the performance of specified functions and relationships thereof. The boundaries of these functional building blocks have often been defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIGS. 4 and 5. It would also be possible to just perform a subset of the steps, e.g., just steps 404-420, in order to determine whether one or more R-R intervals within a group or set of R-R intervals is/are false R-R interval(s), or more specifically, R-R intervals(s) associated with R-wave undersensing or AV conduction block. For another example, it is possible to change the boundaries of some of the blocks shown in FIG. 7.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiments of the present technology without departing from its scope. While the dimensions, types of materials and coatings described herein are intended to define the parameters of the embodiments of the present technology, they are by no means limiting and are exemplary embodiments. Many other embodiments will be apparent to those of skill in the art upon reviewing the above description. The scope of the embodiments of the present technology should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. A method for use by a device or system that monitors cardiac activity, the method comprising:
   obtaining information for at least three R-R intervals included in a window leading up to a detection of a potential arrhythmic episode, wherein each of the R-R intervals has a respective duration, and each of the R-R intervals is either a true R-R interval or a false R-R interval;
   classifying one of the R-R intervals as being a false R-R interval, in response to both
      (i) determining that the duration of the one of the R-R intervals is greater than a first specified threshold, and
      (ii) determining that the duration of the one of the R-R intervals is within a second specified threshold of being an integer multiple of at least X of the other R-R intervals for which information is obtained, wherein the integer multiple is at least 2, and wherein X is a specified integer that is 1 or greater; and
   using results of the classifying to determine that the potential arrhythmic episode is a false positive detection.

2. The method of claim 1, wherein the other R-R intervals, which are used in the (ii) determining that the duration of the one of the R-R intervals is within the second specified threshold of being an integer multiple of at least X of the other R-R intervals, comprise at least N neighboring R-R intervals, wherein N is a specified integer that is 6 or greater, and N is greater than X.

3. The method of claim 2, wherein the at least N neighboring R-R intervals includes at least M immediately preceding R-R intervals and at least M immediately following R-R intervals, where M is a specified integer that is 3 or greater.

4. The method of claim 2, wherein the (ii) determining that the duration of the R-R interval is within the second specified threshold of being an integer multiple of a duration of at least X neighboring R-R interval(s), comprises for each said neighboring R-R interval of the at least X neighboring R-R interval(s):
   determining a ratio of the duration of the R-R interval to the duration of the neighboring R-R interval;
   rounding the ratio to its closest integer to produce a rounded ratio;
   determining that the rounded ratio has a value of at least 2;
   determining an indication of a difference between the R-R interval and the rounded ratio that has the value of at least 2; and
   determining that the indication of the difference between the R-R interval and the rounded ratio is within a difference threshold that comprises the second specified threshold.

5. The method of claim 1, wherein the first specified threshold is 600 ms, and the (i) determining that the duration of the one of the R-R intervals is greater than the first specified threshold comprises determining that the duration of the one of the R-R intervals is greater than 600 ms.

6. The method of claim 1, wherein the using results of the classifying to determine that the potential arrhythmic episode is a false positive comprises:
   determining that at least a threshold amount of the R-R intervals, within the window leading up to the detection of the potential arrhythmic episode, are classified as being a false R-R interval; and
   the using results of the classifying to determine that the potential arrhythmic episode is a false positive detection is also based on determining that at least the threshold amount of the R-R intervals, within the window leading up to the detection of the potential arrhythmic episode, are classified as being a false R-R interval.

7. The method of claim 6, wherein the potential arrhythmic episode comprise a potential AF or VF episode, and wherein the using results of the classifying to determine that the potential AF or VF episode is a false positive also comprises:
   removing, from the window leading up to the detection of the potential AF or VF episode, all of the R-R intervals that are classified as being false R-R intervals;
   determining for the R-R intervals remaining in the window, after the removing, a median indicator of an interval-to-interval difference; and
   determining that the potential AF or VF episode is a false positive based on the median indicator of an interval-to-interval difference being less than a further specified threshold.

8. The method of claim 1, further comprising:
   grouping the at least three R-R intervals included in the window into two or more groups based on the durations of the R-R intervals, such that R-R intervals that are within a third specified threshold of one another are grouped into a same one of the groups; and
   classifying one of the groups that includes a greatest number of R-R intervals as a dominant group;
   wherein the other R-R intervals, which are used in the (ii) determining that the duration of the one of the R-R intervals is within the second specified threshold of being an integer multiple of at least X of the other R-R intervals, comprise R-R intervals within the dominant group.

9. The method of claim 8, wherein:
   the grouping results in a histogram including a plurality of bins, each of which corresponds to one of the groups that include R-R intervals that are within the third specified threshold of one another; and
   the classifying one of the groups as the dominant group is performed by identifying the group corresponding to the bin of the histogram that has a greatest number of R-R intervals therein.

10. A device, comprising:
   one or more electrodes;
   a sensing circuit coupled to the one or more electrodes and configured to obtain a signal indicative of cardiac electrical activity; and
   at least one of a processor or controller configured to
      determine, based on the signal indicative of cardiac electrical activity, information for at least three R-R intervals included in a window of the signal leading up to a detection of a potential arrhythmic episode, wherein each of the R-R intervals has a respective duration, and each of the R-R intervals is either a true R-R interval or a false R-R interval,
      determine for each R-R interval, of at least a threshold amount of the R-R intervals, that the duration of the R-R interval is greater than a first specified threshold, that the duration of the R-R interval is within a second specified threshold of being an integer multiple of at least X of the other R-R intervals for which information is obtained, wherein the integer multiple is at least 2, and wherein X is a specified integer that is 1 or greater, and that the R-R interval is classified as being a false R-R interval, based on the duration of the R-R interval being greater than the first specified threshold, and based on the duration of the R-R interval being within the second specified threshold of being an integer multiple of at least X of the other R-R intervals for which information is obtained, and
      determine that the potential arrhythmic episode is a false positive based on the at least the threshold amount of the R-R intervals, within the window leading up to the detection of the potential arrhythmic episode, being classified as being a false R-R interval.

11. The device of claim 10, wherein the other R-R intervals, which are used to determine that the duration of one of the R-R intervals is within the second specified threshold of being an integer multiple of at least X of the other R-R intervals, comprise at least N neighboring R-R intervals, wherein N is a specified integer that is 6 or greater, and N is greater than X.

12. The device of claim 11, wherein the at least N neighboring R-R intervals includes at least M immediately preceding R-R intervals and at least M immediately following R-R intervals, where M is a specified integer that is 3 or greater.

13. The device of claim 11, wherein in order to determine that the duration of the R-R interval is within the second specified threshold of being an integer multiple of a duration of at least X neighboring R-R interval(s), the at least one of the processor or controller is/are configured to perform the following for each said neighboring R-R interval of the at least X neighboring R-R interval(s):
   determine a ratio of the duration of the R-R interval to the duration of the neighboring R-R interval;
   round the ratio to its closest integer to produce a rounded ratio;
   determine that the rounded ratio has a value of at least 2;
   when the rounded ratio has a value of at least 2, determine an indication of a difference between the R-R interval and the rounded ratio that has the value of at least 2; and
   determine that the indication of the difference between the R-R interval and the rounded ratio is within a difference threshold that comprises the second specified threshold.

14. The device of claim 10, wherein the potential arrhythmic episode comprise a potential AF or VF episode, and wherein the at least one of the processor or controller is/are configured to:
   remove, from the window leading up to the detection of the potential AF or VF episode, all of the R-R intervals that are classified as being a false R-R interval to thereby produce a corrected window;
   determine for the R-R intervals remaining in the window, after the removing, a median indicator of an interval-to-interval difference; and
   determine that the potential AF or VF episode is a false positive also based on the median indicator of the interval-to-interval difference being less than a further specified threshold.

15. The device of claim 10, wherein the at least one of the processor or controller is/are configured to:
   group the at least three R-R intervals included in the window into two or more groups based on the durations of the R-R intervals, such that R-R intervals that are within a third specified threshold of one another are grouped into a same one of the groups; and
   classify one of the groups that includes a greatest number of R-R intervals as a dominant group;
   wherein the other R-R intervals, which are used to determine that the duration of the one of the R-R intervals is within the second specified threshold of being an integer multiple of at least X of the other R-R intervals, comprise R-R intervals within the dominant group.

16. The device of claim 10, wherein the device comprises an implantable medical device (IMD) including a telemetry circuit configured to enable the IMD to communicate with an external device that is coupled to a patient care network, and memory configured to store data corresponding to one or more arrhythmic episodes detected by the IMD, and wherein the at least one of a processor or controller is/are further configured to at least one of:
   prevent transmission by the telemetry circuit, to the external device that is communicatively coupled to the patient care network, of data corresponding to a potential arrhythmic episode that is detected by the IMD but is thereafter determined by the IMD as being a false positive detection;
   allow overwriting in the memory of data corresponding to a potential arrhythmic episode that was detected by the IMD but is thereafter determined by the IMD as being a false positive detection; or
   prevent storing in the memory of data corresponding to a potential arrhythmic episode that is detected by the IMD but is thereafter determined by the IMD as being a false positive detection.

17. A method for determining whether to classify a detection of a potential atrial fibrillation (AF) or ventricular fibrillation (VF) episode as a false positive detection, comprising:
   obtaining information for R-R intervals including in a window leading up to the detection of the potential AF or VF episode, wherein each of the R-R intervals has a respective duration, and each of the R-R intervals is either a true R-R interval or a false R-R interval;
   for each R-R interval of a plurality of the R-R intervals included in the window, classifying the R-R interval as being a false R-R interval associated with R-wave undersensing or AV conduction block, in response to both
      determining that the duration of the R-R interval is greater than a first specified threshold, and
      determining that the duration of the R-R interval is within a second specified threshold of being an integer multiple of at least X of the other R-R intervals for which information is obtained, wherein the integer multiple is at least 2, and wherein X is a specified integer that is 1 or greater; and
   classifying the detection of the potential AF or VF episode as a false positive detection, in response to both
      at least a first threshold amount of the R-R intervals, within the window leading up to the detection of the potential AF or VF episode, being classified as being a false R-wave associated with R-wave undersensing or AV conduction block, and
      a median indicator of an interval-to-interval difference, of R-R intervals within the window that are not classified as being a false R-wave associated with R-wave undersensing or AV conduction block, being greater than a further specified threshold.

18. The method of claim 17, wherein the method is performed by an implantable medical device (IMD), and the method further comprising at least one of the following:
   the IMD preventing transmitting, to an external device that is communicatively coupled to a patient care network, data corresponding to a potential AF or VF episode that is detected by the IMD but is thereafter determined by the IMD as being a false positive detection;
   the IMD allowing overwriting of stored data corresponding to the potential AF or VF episode that was detected by the IMD but is thereafter determined by the IMD as being a false positive detection; or
   the IMD not storing in memory data corresponding to the potential AF or VF episode that is detected by the IMD but is thereafter determined by the IMD as being a false positive detection.

19. A device, comprising:
   one or more electrodes;
   a sensing circuit coupled to the one or more electrodes and configured to obtain a signal indicative of cardiac electrical activity; and
   at least one of a processor or controller configured to determine, based on the signal indicative of cardiac electrical activity, information for R-R intervals including in a window leading up to a detection of a potential atrial fibrillation (AF) or ventricular fibrillation (VF) episode, wherein each of the R-R intervals has a respective duration, and each of the R-R intervals is either a true R-R interval or a false R-R interval;

for each R-R interval of a plurality of the R-R intervals included in the window, classify the R-R interval as being a false R-R interval associated with R-wave undersensing or AV conduction block, in response to both the duration of the R-R interval being greater than a first specified threshold, and the duration of the R-R interval being within a second specified threshold of being an integer multiple of at least X of the other R-R intervals for which information is obtained, wherein the integer multiple is at least 2, and wherein X is a specified integer that is 1 or greater; and classify the detection of the potential AF or VF episode as a false positive detection, in response to both at least a first threshold amount of the R-R intervals, within the window leading up to the detection of the potential AF or VF episode, being classified as being a false R-wave associated with R-wave undersensing or AV conduction block, and a median indicator of an interval-to-interval difference, of R-R intervals within the window that are not classified as being a false R-wave associated with R-wave undersensing or AV conduction block, being greater than a further specified threshold.

20. The device of claim 19, wherein the device comprises an implantable medical device (IMD) including a telemetry circuit configured to enable the IMD to communicate with an external device, and memory configured to store data corresponding to one or more arrhythmic episodes detected by the IMD, and wherein the at least one of a processor or controller is/are further configured to at least one of:

prevent transmission by the telemetry circuit, to an external device that is communicatively coupled to a patient care network, of data corresponding to the potential AF or VF episode that is detected by the IMD but is thereafter determined by the IMD as being a false positive detection;

allow overwriting in the memory of data corresponding to the potential AF or VF episode that was detected by the IMD but is thereafter determined by the IMD as being a false positive detection; or prevent storing in the memory of data corresponding to the potential AF or VF episode that is detected by the IMD but is thereafter determined by the IMD as being a false positive detection.

\* \* \* \* \*